(12) United States Patent
Krieg et al.

(10) Patent No.: US 6,214,806 B1
(45) Date of Patent: Apr. 10, 2001

(54) USE OF NUCLEIC ACIDS CONTAINING UNMETHYLATED CPC DINUCLEOTIDE IN THE TREATMENT OF LPS-ASSOCIATED DISORDERS

(75) Inventors: Arthur M. Krieg; David A. Schwartz, both of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/030,701

(22) Filed: Feb. 25, 1998

Related U.S. Application Data

(60) Provisional application No. 60/039,405, filed on Feb. 28, 1997.

(51) Int. Cl.[7] ................................................. A61K 31/70
(52) U.S. Cl. ........................................................... 514/44
(58) Field of Search ............................... 514/44; 536/24.3, 536/24.5, 23.1, 25.6

(56) References Cited

U.S. PATENT DOCUMENTS

| | | |
|---|---|---|
| 3,906,092 | 9/1975 | Hilleman et al. . |
| 4,469,863 | 9/1984 | Ts'o et al. . |
| 5,023,243 | 6/1991 | Tullis ..................................... 514/44 |
| 5,248,670 | 9/1993 | Draper et al. ......................... 514/44 |
| 5,580,859 | 12/1996 | Felgner et al. ........................ 514/44 |
| 5,585,479 | 12/1996 | Hoke et al. .......................... 536/24.5 |
| 5,589,466 | 12/1996 | Felgner et al. ........................ 514/44 |
| 5,663,153 | 9/1997 | Hutcherson et al. .................. 514/44 |
| 5,679,647 | 10/1997 | Carson et al. ......................... 514/44 |
| 5,723,335 | 3/1998 | Hutcherson et al. ................ 435/375 |
| 5,786,189 | 7/1998 | Locht et al. ....................... 435/172.3 |
| 5,804,566 | 9/1998 | Carson et al. ......................... 514/44 |
| 5,830,877 | 11/1998 | Carson et al. ......................... 514/44 |
| 5,849,719 | 12/1998 | Carson et al. ......................... 514/44 |

FOREIGN PATENT DOCUMENTS

| | | |
|---|---|---|
| 0 092 574 B1 | 4/1983 | (EP) . |
| 0468520 A3 | 1/1992 | (EP) . |
| 0302758 B1 | 3/1994 | (EP) . |
| WO 91/12811 | 9/1991 | (WO) . |
| WO 92103456 | 3/1992 | (WO) . |
| WO 92/18522 | 10/1992 | (WO) . |
| WO 92/21353 | 12/1992 | (WO) . |
| 94/02646 * | 2/1994 | (WO) . |
| WO 94/19945 | 9/1994 | (WO) . |
| WO 95/05853 | 3/1995 | (WO) . |
| WO 95/26204 | 10/1995 | (WO) . |
| 96/02555 * | 2/1996 | (WO) . |
| 96/02560 * | 2/1996 | (WO) . |
| WO 96/02555 | 2/1996 | (WO) . |
| WO 96/35782 | 11/1996 | (WO) . |
| 96/40162 * | 12/1996 | (WO) . |
| WO 97/28259 | 8/1997 | (WO) . |
| WO 98/14210 | 4/1998 | (WO) . |
| WO 98/5545 | 12/1998 | (WO) . |
| WO 98/55609 | 12/1998 | (WO) . |
| WO 98/37919 | 1/1999 | (WO) . |

OTHER PUBLICATIONS

Schenker et al. (1998) Respiratory Health hazards in Agriculture. Am. J. Respiratory and Critical Care Med. 158: S1–S76.*

Nyce, J.W., et al., "DNA antisense therapy for asthma in an animal model", Nature, 385:721–725 (1997).

Adya N et al., Expansion of CREB's DNA recognition specificity by Tax results from interaction with Ala–Ala–Arg at positions 282–284 near the conserved DNA–binding domain of CREB. Proc Natl Acad Sci USA 91(12):5642–6, Jun. 7, 1994.

Angier, N., Microbe DNA Seen as Alien By Immune System, New York Times, Apr. 11, 1995.

Azad RF et al., Antiviral Activity of a Phosphorothioate Oligonucleotide Complementary to RNA of the Human Cytomegalovirus Major Immediate–Early Region. Antimicrobial Agents and Chemotherapy, 37:1945–1954, Sep., 1993.

Azuma, Biochemical and Immunological Studies on Cellular Components of Tubercle Bacilli, Kekkaku, vol. 69, 9:45–55, 1992.

Ballas ZK et al., Induction of NK activity in murine and human cells by CpG motifs in oligodeoxynucleotides and bacterial DNA. J Immunol 157(5):1840–5, 1996.

Bayever, E., Systemic Administration of a Phosphorothioate Oligonucleotide with a Sequence Complementary to p53 for Acute Myelogenous leukemia and Myelodysplastic Syndrome: Initial Results of a Phase I Trial, Antisense Res. & Dev. (1993), 3:383–390.

Bennett RM et al., DNA binding to human leukocytes. Evidence for a receptor–mediated association, internalization, and degradation of DNA. J Clin Invest 76(6):2182–90, 1985.

Berg DJ et al., Interleukin–10 is a central regulator of the response to LPS in murine models of endotoxic shock and the Shwartzman reaction but not endotoxin tolerance. J Clin Invest 96(5):2339–47, 1995.

(List continued on next page.)

Primary Examiner—George C. Elliott
Assistant Examiner—Thomas G. Larson
(74) Attorney, Agent, or Firm—Wolf, Greenfield & Sacks, P.C.

(57) ABSTRACT

The present invention is based on the finding that nucleic acids containing at least one unmethylated cytosine-guanine (CpG) dinucleotide affect immune responses in a subject. These nucleic acids containing at least one unmethylated cytosine-guanine (CpG) dinucleotide can be used to treat pulmonary disorders having an immunologic component, such as a response to inhaled lipopolysaccharide. The invention provides methods of treating subjects who have or are at risk of having these pulmonary disorders, and methods of altering the immunological components of the pulmonary disorders. The invention also provides pharmaceutical compositions for treating pulmonary disorders that have an immunologic component.

43 Claims, 11 Drawing Sheets

OTHER PUBLICATIONS

Blanchard DK et al., Interferon–gamma induction by lipopolysaccharide: dependence on interleukin 2 and macrophages. *J Immunol* 136(3):963–70, 1986.

Blaxter et al., Genes expressed in Brugia malayi infective third stage larvae. *Molecular and Biochemical Parasitology*, 77:77–93. 1996.

Boggs RT et al., Characterization and modulation of immune stimulation by modified oligonucleotides. *Antisense Nucleic Acid Drug Dev* 7(5):461–71, Oct. 1997.

Branda RF et al., Amplification of antibody production by phosphorothioate oligodeoxynucleotides. *J. Lab Clin Med* 128(3):329–38, Sep. 1996.

Branda et al., Immune Stimulation by an Antisense Oligomer Complementary to the rev gene of HIV–1. *Biochemical Pharmacology*, vol. 45, 10:2037–2043, 1993.

Chace, J. et al., Regulation of Differentiation in CD5+ and Conventional B Cells, *Clinical Immunology and Immunopathology*, (1993), 68:3:327–332.

Chang YN et al., The palindromic series I repeats in the simian cytomegalovirus major immediate–early promoter behave as both strong basal enhancers and cyclic AMP response elements. *J Virol* 64(1):264–77, Jan. 1990.

Chu RS et al., CpG oligodeoxynucleotides act as adjuvants that switch on T helper 1 (Th1) immunity. *J Exp Med* 186(10):1623–31, Nov. 17, 1997.

Crosby et al., The Early Responses Gene FGFI–C Encodes a Zinc Finger Transcriptional Activator and is a Member of the GCGGGGGCG (GSG) Element–Binding Protein Family. *Mol. Cell. Biol.*, 2:3835–3841, 1991.

Crystal, Transfer of Genes to Humans: Early Lessons and Obstacles to Success. *Science*, vol. 270, pp. 404–410, 1995.

D'Andrea A et al., Interleukin 10 (IL–10) inhibits human lymphocyte interferon gamma–production by suppressing natural killer cell stimulatory factor/IL–12 synthesis in accessory cells. *J Exp Med* 178(3):1041–8, 1993.

Englisch et al., Chemically Modified Oligonucleotides as Probes and Inhibitors, *Angew. Chem. Int. Ed. Engl.*, 30:613–629, 1991.

Erb KJ et al., Infection of mice with *Mycobacterium bovis–Bacillus Calmette–Guerin* (BCG) suppresses allergen–induced airway eosinophilia. *J Exp Med* 187(4):561–9, Feb. 16, 1998.

Etlinjer, Carrier sequence selection—one key to successful vaccines, *Immunology Today*, vol. 13, 52–55, 1992.

Fox RI, Mechanism of action of hydroxychloroquine as an antirheumatic drug. *Chemical Abstracts*, 120:15, Abstract No. 182630 (Apr. 29, 1994).

Gura, T., Antisense Has Growing Pains. *Science* (1995), 270:575–576.

Hadden J et al., Immunostimulants. *TIPS*, (1993), 141:169–174.

Hadden J et al., Immunopharmacology, *JAMA*, (1992) 268:20:2964–2969.

Halpern MD et al., Bacterial DNA induces murine interferon–gamma production by stimulation of interleukin–12 and tumor necrosis factor–alpha. *Cell Immunol* 167(1):72–8, 1996.

Hatzfeld J., Release of Early Human Hematopoietic Progenitors from Quiescence by Antisense Transforming Growth Factor β1 or Rb Oligonucleotides, *J. Exp. Med.*, (1991) 174:925–929.

Highfield PE, Sepsis: the More, the Murkier. *Biotechnology*, 12:828, Aug. 12, 1994.

Hoeffler JP et al., Identification of multiple nuclear factors that interact with cyclic adenosine 3',5'–monophosphate response element–binding protein and activating transcription factor–2 by protein–protein interactions. *Mol Endocrinol* 5(2):256–66, Feb. 1991.

Iguchi–Ariga SM and Shaffner W, CpG methylation of the cAMP–responsive enhancer/promoter sequence TGACGTCA abolishes specific factor binding as well as transcriptional activation. *Genes Dev* 3(5):612–9, May 1989.

Iverson, P., et al., "Pharmacokinetics of an Antisense Phosphorothioate Oligodeoxynucleotide against reve from Human Immunodeficiency Virus Type 1 in the Adult male Rate Following Single Injections and Continuous Infusion", *Antisense Research and Development*, (1994), 4:43–52.

Ishikawa R et al., IFN induction and associated changes in splenic leukocyte distribution. *J Immunol* 150(9):3713–27, May 1, 1993.

Kataoka T et al., Antitumor Activity of Synthetic Oligonucleotides with Sequences from cDNA Encoding Proteins of *Myobcteriunm bovis* BCG. *Jpn. J. Cancer Res.*, 83:244–247, Mar. 1992.

Kimura Y et al., Binding of Oligoguanylate to Scavenger Receptors Is Required for Oligonucleotides to Augment NK Cell Activity and Induce IFN, *J. Biochem.*, vol. 116, 5:991–994, 1994.

Kline JN et al., CpG motif oligonucleotides are effective in prevention of eosinophilic inflammation in a murine model of asthma. *J Invest Med* 44(7):380A, 1996.

Kline JN et al., Immune redirection by CpG oligonucleotides. Conversion of a Th2 response to a Th1 response in a murine model of asthma. *J Invest Med* 45(3):282A, 1997.

Kline JN et al., CpG oligonucleotides can reverse as well as prevent Th2–mediated inflammation in a murine model of asthma. *J Invest Med* 45(7):298A, 1997.

Klinman DM et al., CpG motifs present in bacteria DNA rapidly induce lymphocytes to secrete interleukin 6, interluekin 12, and interferon gamma. *Proc Natl Acad Sci USA* 93(7):2879–83, 1996.

Krieg AM, An innate immune defense mechanism based on the recognition of CpG motifs in microbial DNA. *J Lab Clin Med* 128(2):128–33, 1996.

Krieg AM et al., Uptake of oligodeoxyribonucleotides by lymphoid cells is heterogeneous and inducible. *Antisense Res Dev* 1(2):161–71, Summer 1991.

Krieg AM et al., Oligodeoxynucleotide modifications determine the magnitude of B cell stimulation by CpG motifs. *Antisense Nucleic Acid Drug Dev* 6(2):133–9, Summer 1996.

Krieg AM et al., "Modification of antisense phosphodiester oligodeoxynucleotides by a 5' cholesteryl moiety increases cellular association and improves efficacy", *Proc. Natl. Acad. Sci.*, (1993), 90:1048–1052.

Krieg AM et al., "CpG DNA: A Pathogenic Factor in Systemic Lupus Erythematosus?", *Journal of Clinical Immunology*, (1995) 15:6:284–292.

Krieg AM et al, Phosphorothioate Oligodeoxynucleotides: Antisense or Anti–Protein?, *Antisense Research and Development*, (1995), 5:241.

Krieg AM et al., "Leukocyte Stimulation by Oligodexoynucleotides", *Applied Antisense Oligonucleotide Technology*, (1998), 431–448.

Krieg AM et al., CpG motifs in bacterial DNA trigger direct B–cell activation. *Nature* 374:546–9, 1995.

Krieg AM et al, "The role of CpG dinuleotides in DNA vaccines", Trends in Microbiology, vol. 6, pp. 23–27, Jan. 1998.

Krieg AM el al, A Role for Endogenous Retroviral Sequences in the Regulation of Lymphocyte Activation, the Journal of Immunology, vol. 143, 2448–2451, Oct., 1989.

Kuramoto et al., Oligonucleotide Sequences Required for Natural Killer Cell Activation, *Jpn. J. Cancer Res.*, 83:1128–1131, Nov. 1992.

Leonard et al., Conformation of Guanine 8–Oxoadenine Base Pairs in the Crystal Structure of d(CGCGAATT(08A)GCG). *Biochemistry*, 31(36):8415–8420, 1992.

Macfarlane DE and Manzel L, Antagonsim of immunostimulatory CpG–oligodeoxynucleotides by quinacrine, chloroquine, and structurally related compounds. *J Immunol* 160(3):1122–31, Feb. 1, 1998.

Mastrangelo et al. *Seminars in Oncology.* vol. 23, 1:4–21, 1996.

Matson S and Krieg AM, Nonspecific suppression of [3H] thymidine incorporation by "control" oligonucleotides. *Antisense Res Dev* 2(4):325–30, Winter 1992.

Messina et al., The Influence of DNA Structure on the in vitro Stimulation of Murine Lymphocytes by Natural and Synthetic Polynucleotide Antigens. *Cellular Immunology,* 147:148–157, 1993.

Messina et al., Stimulation of in vitro Murine Lymphocyte Proliferation by Bacterial DNA. *J. Immunol.,* vol. 147, 6:1759–1764, Sep. 15, 1991.

Mojcik, C., et al., "Administration of a Phosphorothioate Oligonucleotide Antisense Murine Endogenous Retroviral MCF env Causes Immune Effect in vivo in a Sequence–Specific Manner", *Clinical Immunology and Immunopathology,* (1993), 67:2:130–136.

Mottram et al., A novel CDC2–related protein kinase from leishmania mexicana LmmCRK1 is post–translationally regulated during the life cycle. *J. Biol. Chem.* 268:28, 21044–21052 (Oct. 1993).

Pisetsky, D., "Stimulation of in vitro proliferation of murine lymphocytes by synthetic oligodeoxynucleotides", *Molecular Biology Repairs,* (1993) 18:217–221.

Quddus J et al., Treating activated CD4+ T cells with either of two distinct DNA methyltransferase inhibitors, 5–azacytidine or procainamide, is sufficient to cause a lupus–like disease in syngeneic mice. *J Clin Invest* 92(1):38–53, Jul. 1993.

Rojanasakul Y., Antisense oligonucleotide therapeutics: drug delivery and targeting. *Advanced Drug Delivery Reviews,* 18:115–131, 1996.

Roman M et al., Immunostimulatory DNA sequences function as T helper–1–promoting adjuvants. *Nat Med* 3(8):849–54, Aug. 1997.

Sato et al., Immunostimulatory DNA Sequences Necessary for Effective Intradermal Gene Immunization, *Science,* vol. 273, pp. 352–354, 1996.

Schnell et al., Identification and characterization of a *Saccharomyces cerevisiae* gene (PAR1) conferring resistance to iron chelators. *Eur. J. Biochem.,* 200:487–493.

Schwartz DA et al., Endotoxin responsiveness and grain dust–induced inflammation in the lower respiratory tract. *Am J Physiol* 267(5 Pt 1):L609–17, 1994.

Schwartz DA et al., The role of endotoxin in grain dust–induced lung disease. *Am J Respir Crit Care Med* 152(2):603–8, 1995.

Schwartz DA et al., CpG motifs in bacterial DNA cause inflammation in the lower respiratory tract. *J Clin Invest* 100(1):68–73, Jul. 1, 1997.

Shirakawa T et al., The inverse association between tuberculin responses and atopic disorder. *Science* 275(5296):77–9, Jan. 3, 1997.

Sparwasser T et al., Macrophages sense pathogens via DNA motifs: induction of tumor necrosis factor–alpha–mediated shock. *Eur J Immunol* 27(7):1671–9, Jul. 1997.

Stein CA et al., Oligonucleotides as inhibitors of gene expression: a review. *Cancer Research,* 48:2659–2668, 1988.

Stull et al., Antigene, Ribozyme, and Aptamer Nucleic Acid Drugs: Progress and Prospects, *Pharmaceutical Res.,* vol. 12, 4:465–483, 1995.

Subramanian et al., Theoretical Considerations on the "Spine of Hydration" in the Minor Groove of d(CGCGAAT-TCGCG) d(GCGCTTAAGCGC): Monte Carlo Computer Simulation. *Proc. Nat'l. Acad. Sci. USA,* 85:1836–1840, 1988.

Tanaka T et al., An antisense Oligonucleotide complementary to a sequence in IG2b increases G2b germline transcripts stimulates B cell DNA synthesis and inhibits immunoglobulin secretion. *J. Exp. Med.,* 175:597–607, 1992.

Thorne PS., Experimental grain dust atmospheres generated by wet and dry aerosolization techniques. *Am J Ind Med* 25(1):109–12, 1994.

Tokunaga T et al., Synthetic Oligonucleotides with Particular Base Sequences form the cDNA Encoding Proteins of *Myobacterium bovis* BCG Induce Interferons and Activate Natural Killer Cells, *Microbiol. Immunol.,* vol. 36, 1:55–66, 1992.

Tokunaga et al., A Synthetic Single–Stranded DNA, Ply (dG, dC), Induces Interferon $\alpha/\beta$ and $-\gamma$, Augments Natural Killer Activity and Suppresses Tumor Growth. *Jpn. J. Cancer Res.,* 79:682–686, Jun. 1988.

Uhlmann et al., Antisense Oligonucleotides: A New Therapeutic Principle. *Chemical Reviews,* 90:543–584, 1990.

Wagner RW, Gene inhibition using antisense oligodeoxynucleotides. *Nature,* 372:L333–335, 1995.

Wallace et al., Oligonucleotide probes for the screening of recombinant DNA libraries. *Methods in Enzymology,* 152:432–442 (1987).

Weiss R., Upping the Antisense Ante: Scientists bet on profits from reverse genetics. *Science,* 139:108–109, 1991.

Whalen R, DNA Vaccines for Emerging Infection Diseases: What If?, *Emerging Infectious Disease,* vol. 2, 3:168–175, 1996.

Wu GY et al., Receptor–mediated gene delivery and expression in vivo. *J. Biol. Chem.,* 263:14621–14624, 1988.

Wu–Pong S., Oligonucleotides: Opportunities for Drug Therapy and Research. *Pharmaceutical Technology,* 18:102–114, 1994.

Yamamoto S et al., DNA from bacteria, but not from vertebrates, induces interferons, activates natural killer cells and inhibits tumor growth. *Microbiol Immunol* 36(9):983–97, 1992.

Yamamoto S et al., In vitro augmentation of natural killer cell activity and production of interferon–alpha/beta and— gamma with deoxyribonucleic acid fraction from *Mycobacterium bovis* BCG. *Jpn J Cancer Res* 79:866–73, Jul. 1988.

Yamamoto S., Mode of Action of Oligonucleotide Fraction Extracted from *Mycobacterium bovis* BCG, *Kekkaku,* vol. 69, 9:29–32, 1994.

Yamamoto S et al., Unique Palindromic Sequences in Synthetic Oligonucleotides are Required to Induce INF and Augment INF–Mediated Natural Killer Activity. *J. Immunol.*, vol. 148, 12:4072–4076, Jun. 15, 1992.

Yamamoto et al., Lipofection of Synthetic Oligodeoxyribonucleotide Having a Palindromic Sequence AACGTT to Murine Splenocytes Enhances Interferon Production and Natural Killer Activity. *Microbiol. Immunol.*, vol. 38, 10:831–836, 1994.

Yamamoto T et al., Synthetic Oligonucleotides with Certain Palindromes Stimulate Interferon Production of Human Peripheral Blood Lymphocytes in vitro. *Jpn. J. Cancer Res.*, 85:775–779, 1994.

Zhao Q et al., Comparison of cellular binding and uptake of antisense phosphodiester, phosphorothioate, and mixed phosphorothioate and methylphosphonate oligonucleotides. *Antisense Res Dev* 3(1):53–66, Spring 1993.

Zhao Q et al., Stage–specific oligonucleotide uptake in murine bone marrow B–cell precursors. *Blood* 84(11):3660–6, Dec. 1, 1994.

*Biolabs 1988–1989 Catalog.*

Pisetsky et al., Stimulation of Murine Lymphocyte Proliferation by a Phosphorothioate Oligonucleotide with Antisense Activity for Herpes Simplex Virus. *Life Science*, vol. 54, pp. 101–107 (1994).

Pisetsky, The Immunological Properties of DNA, *The Journal of Immunology*, pp. 421–423 (1996).

Pisetsky, Immunological Consequences of Nucleic Acid Therapy, *Antisense Research and Development*, 5:219–225 (1995).

Yi, Ae–Kyung et al., IFN–γ Promotes IL–6 and IgM Secretion in Response to CpG Motifs in Bacterial DNA and Oligonucleotides, *The Journal of Immunology*, pp. 558–564 (1996).

Yi, Ae–Kyung et al., Rapid Immune Activation by CpG Motifs in Bacterial DNA, *The Journal of Immunology*, pp. 5394–5402 (1996).

Blackman, M., et al., Specific 5' and 3' regions of the μ–chain gene are undermethylated at distinct stages of B–cell differentiation, *Proc. Natl. Acad. Sci*, 82:3809–3813, (1985).

Threadgill, D. S., et al., "Mitogenic synthetic polynucleotides suppress the antibody response4 to a bacterial polysaccharide", *Vaccine*, 16:1:76–82, (1998).

Yamamoto, T., et al., "Ability of Oligonucleotides with Certain Palindromes to Induce Interferon Production and Augment Natural Killer Cell Activity Is Associated with Their Base Length", *Antisense Research And Development*, 4:119–122 (1994).

Yi et al., "IFN–γ Promotes IL–6 and IgM Secretion in response to CpG Motifs in Bacterial DNA and Oligodeoxynucleotides," *J. Immunology*, Jan. 15, 1996, vol. 156, No. 2, pp. 558–564.

Blackman et al., "Specific 5' and 3' regions of the μ–chain gene are undermethylated at distinct stages of B–cell differentiation," *Proc. Natl. Acad. Sci.*, Jun. 1985, vol. 82, pp. 3809–3813.

Threadgill et al., "Mitogenic synthetic polynucleotides supress the antibody response to a bacterial polysaccharide," *Vaccine*, Jan. 1998, vol. 16, No. 1, pp. 76–82.

Branda et al., "Amplification of antibody production by phosphorothioate oligodeoxynucleotides," *J. Lab. Clin. Med.*, Sep. 1996, vol. 128, No. 3, pp. 329–338.

* cited by examiner

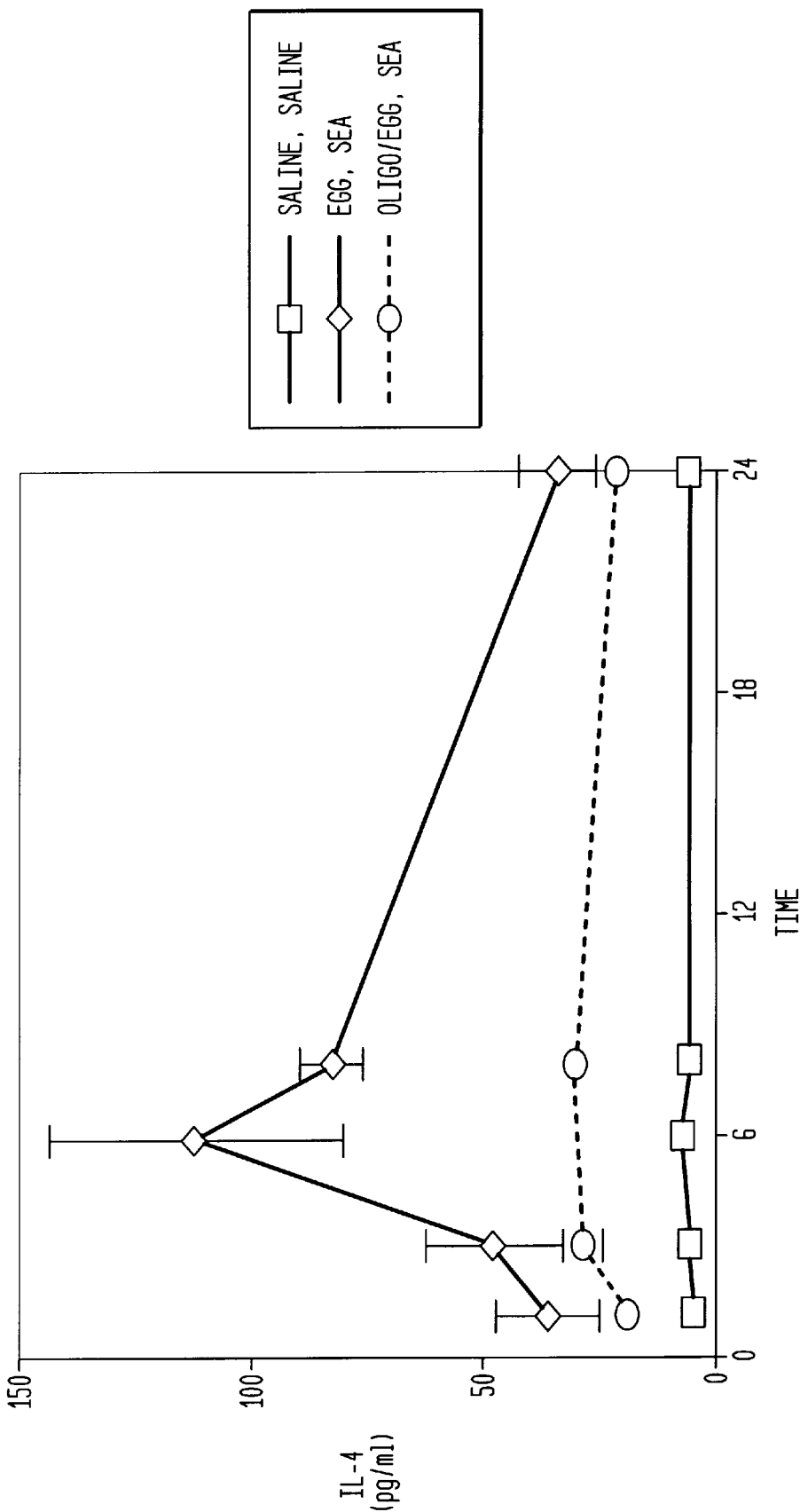

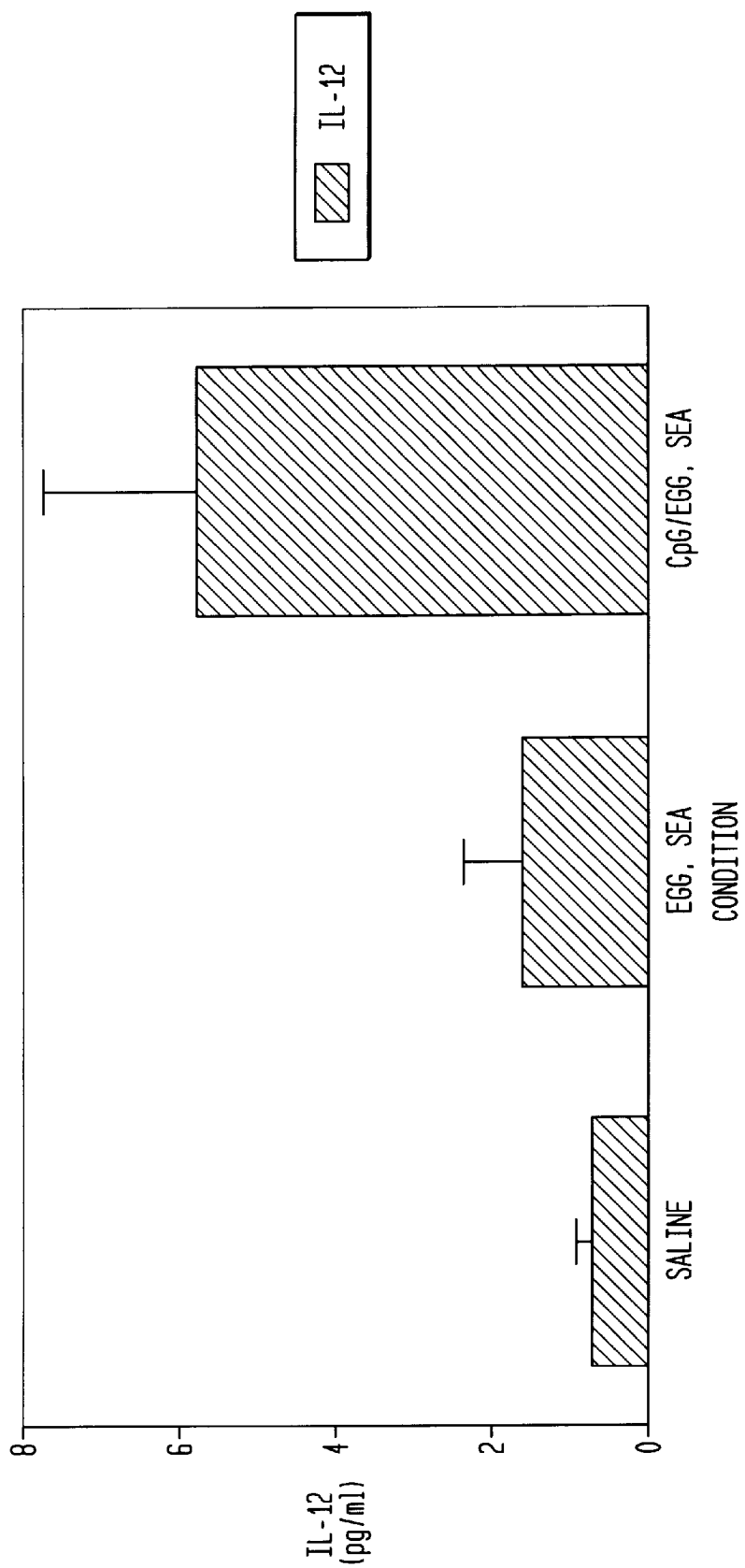

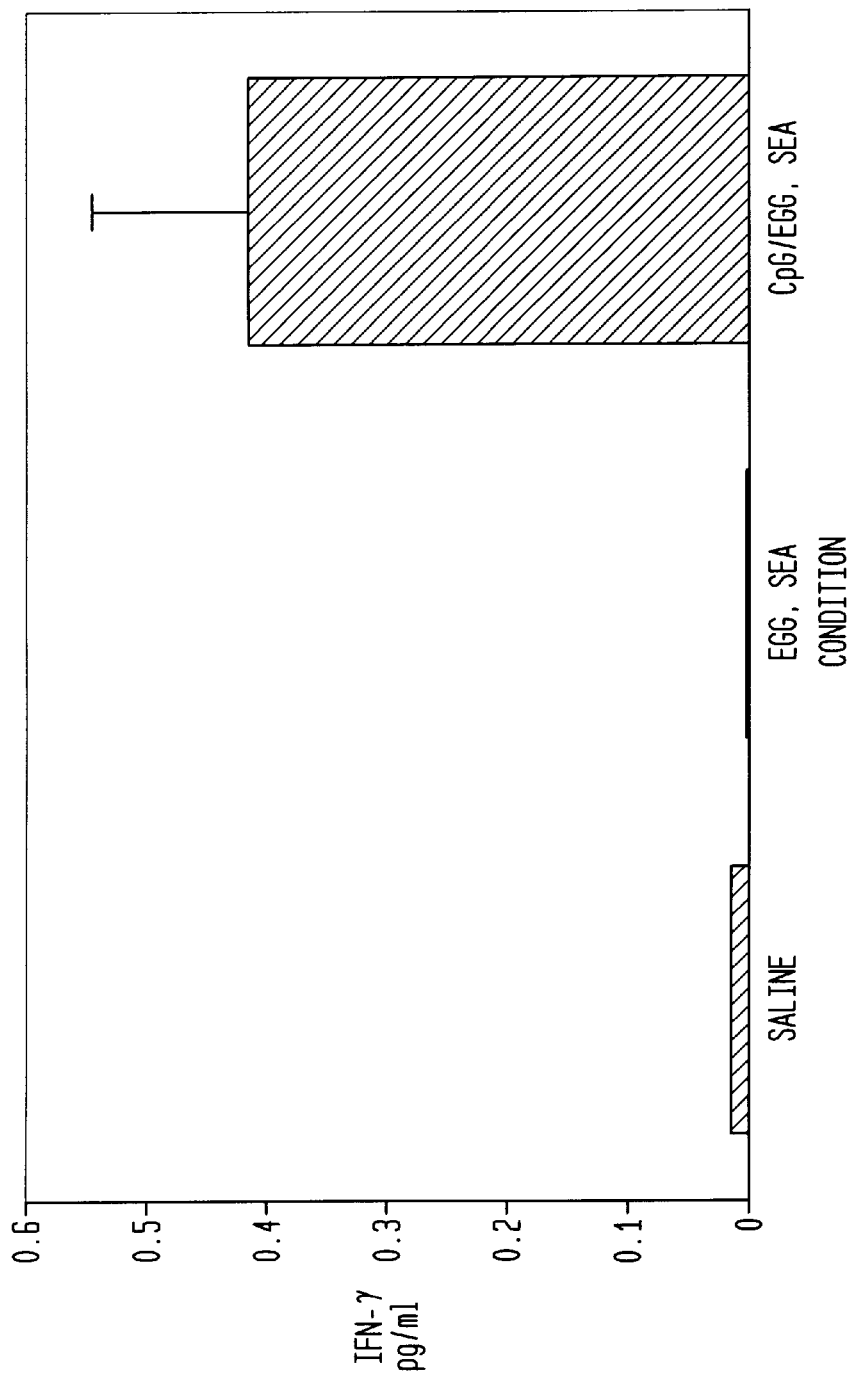

USE OF NUCLEIC ACIDS CONTAINING UNMETHYLATED CPC DINUCLEOTIDE IN THE TREATMENT OF LPS-ASSOCIATED DISORDERS

CROSS REFERENCE TO RELATED APPLICATIONS

This application claims priority under 35 USC §119(e)(1) from provisional application Ser. No. 60/039,405, filed Feb. 28, 1997.

FIELD OF THE INVENTION

This invention relates to generally to pulmonary disorders, and specifically to the use of oligonucleotides having at least one unmethylated CpG dinucleotide (CpG ODN) in the treatment of such disorders.

BACKGROUND OF THE INVENTION

Endotoxin is one of the primary mediators of inflammation released by Gram negative organisms and is an important cause of environmentally induced airway disease, such as ARDS. Inhaled endotoxin can cause airflow obstruction in previously unexposed subjects. Inhaled endotoxin is strongly associated with the development of acute decrements in airflow among cotton workers, wine confinement workers, and poultry workers. The concentration of endotoxin in the bioaerosol appears to be the most important occupational exposure associated with the development and progression of airway disease in agricultural workers (Schwartz, D. A., et al., *Am. J. Respir. Crit. Care Med.* 152:603–8, 1995).

In addition to being related to several occupational pulmonary diseases, exposure to endotoxin and to its purified derivative lipopolysaccharide (LPS) is also associated with severe asthma. The concentration of endotoxin in the domestic environment adversely affects asthmatics, with higher concentrations of ambient endotoxin associated with greater degrees of airflow obstruction. In addition, asthmnatic individuals develop airflow obstruction at lower concentrations of inhaled endotoxin than normal controls. Exposure-response studies have shown that inhaled lipopolysaccharide (LPS) produces recruitment of neutrophils, activation of macrophages with production and release of pro-inflammatory cytokines, and damage to airway epithelia in a dose-dependent manner. These studies indicate that endotoxin is an important cause of airway disease among exposed individuals.

The acute respiratory distress syndrome (ARDS) is a condition characterized by acute hypoxemia respiratory failure due to pulmonary edema (reviewed in Honing, E. G., and Ingram, R. H., Jr., in: *Harrison's Principles of Internal Medicine,* 14th Edition, A. S. Fauci, et al. (eds.), McGraw-Hill, N.Y., pp. 1483–1486, 1998; and Goodman, R. B., et al., *Am J. Respir. Crit. Care Med.* 154:602–11, 1996). ARDS represents a spectrum of responses to acute lung injury (ALI); these response occur as complications of a more widespread systemic response to acute inflammation or injury. ALI develops rapidly after a predisposing condition triggers a systemic inflammatory response and is most strongly associated with conditions that produced direct alveolar injury or direct injury via the pulmonary capillary bed, such as aspiration, diffuse infection, toxic inhalation, direct injury to the alveolar epithelium, or sepsis syndrome. ALI is the consequence of unregulated over-expression of usual systemic inflammatory responses to infection and/or injury. Injury involves the alveolar epithelium and the pulmonary capillary endothelium, and results in a complex cascade of events. Injury is produced by cellular events associated with neutrophils, macrophages, monocytes, and lymphocytes producing various cytokines, in turn producing cellular activation, chemotaxis, and adhesion.

Gram-negative infections are a major cause of morbidity and mortality, especially in hospitalized and immunocompromised patients. (Duma, *Am. J. of Med.,* 78 (Suppl. 6A): 154–164, 1985; and Kreger et al., *Am. J. Med.,* 68:344–355, 1980). Although available antibiotics are generally effective in inhibiting growth of Gram-negative bacteria, they do not neutralize the pathophysiological effects associated with endotoxins. Endotoxin is a heat stable bacterial toxin composed of lipopolysaccharides (LPS) released from the outer membrane of Gram-negative bacteria upon lysis (Shenep et al., *J. Infect. Dis.,* 150(3):380–388, 1984), and is a potent stimulator of the inflammatory response. Endotoxemia occurs when endotoxin enters the bloodstream resulting in a dramatic systemic inflammatory response.

The uptake of oligonucleotides by B lymphocytes has been shown to be regulated by LPS-induced cell activation (Krieg, A. M., et al., *Antisense Res. Devel.* 1:161, 1991). Many detrimental in vivo effects of LPS have been shown to result from soluble mediators released by inflammatory cells. (Morrison et al., *Am. J. Pathol.,* 93(2):527–617, 1978). Monocytes and neutrophils, which ingest and kill microorganisms, play a key role in this process. Monocytes and neutrophils respond to endotoxin in vivo by releasing soluble proteins with microbicidal, proteolytic, opsonic, pyrogenic, complement-activating and tissue-damaging effects. These factors mediate many of the pathophysiological effects of endotoxin. For example, tumor necrosis factor (TNF), a cytokine released by endotoxin-stimulated monocytes, causes fever, shock, and alterations in glucose metabolism and is a potent stimulator of neutrophils. Other cytokines such as IL-1, IL-6, and IL-8 also mediate many of the pathophysiologic effects of LPS, as well as other pathways involving endothelial cell activation by tissue factor, kininogen, nitric oxide and complement.

Endotoxin-associated disorders result from extra-gastrointestinal exposure to LPS, e.g., administration of LPS-contaminated fluids, inhalation of LPS, or Gram-negative infections. Endotoxin-associated disorders can also result when the natural cellular barrier is injured and the normal Gram-negative flora breach this barrier. For example, endotoxin-associated disorders can occur (a) when there is ischemia of the gastrointestinal tract (e.g, following hemorrhagic shock or during certain surgical procedures), or (b) when systemic or local inflammation causes increased permeability of the gut or lung to endotoxin or Gram-negative organisms. The presence of endotoxin and the resulting inflammatory response may result, for example, in adult respiratory distress syndrome (ARDS), dust-induced airway disease, and exacerbation of asthma, in addition to endotoxemia, systemic inflammatory response syndrome (SIRS), sepsis syndrome, septic shock, disseminated intravascular coagulation (DIC), cardiac dysfunction, organ failure, liver failure (hepatobiliary dysfunction), brain failure (CNS dysfunction), renal failure, multi-organ failure and shock.

Several therapeutic compounds have been developed to inhibit the toxic effects of endotoxin, including antibacterial LPS-binding agents and anti-LPS antibodies, although each has met with limitations. For example, Polymyxin B (PMB) is a basic polypeptide antibiotic which binds to Lipid A, the most toxic and biologically active component of endotoxin. PMB inhibits endotoxin-mediated activation of neutrophil granule release in vitro and is a potential therapeutic agent for Gram-negative infections. However, because of its systemic toxicity, this antibiotic has limited therapeutic use, and is generally used topically. Combination therapy using antibiotics and high doses of methylprednisolone sodium succinate (MPSS) showed more promise as this regimen prevented death in an experimental animal model of Gram-negative sepsis. However, a clinical study using MPSS with antibiotics in treatment of patients having clinical signs of systemic sepsis showed that mortality rates were not significantly different between the treatment and placebo groups (Bone et al., *N. Engl. J. Med.* 317:653, 1987).

SUMMARY OF THE INVENTION

The present invention is based on the finding that nucleic acids containing at least one unmethylated cytosine-guanine (CpG) dinucleotide affect the immune response in a subject by activating natural killer cells (NK) or redirecting a subject's immune response from a Th2 to a Th1 response by inducing monocytic and other cells to produce Th1 cytokines. These nucleic acids containing at least one unmethylated CpG can be used to treat pulmonary disorders having an immunologic component, such as asthma or environmentally induced airway disease.

In a first embodiment, a method of treating a subject having or at risk of having an acute decrement in air flow by administering a therapeutically effective amount of nucleic acids containing at least one unmethylated CpG is provided.

In another embodiment, a method of treating a subject having or at risk of having an inflammatory response to lipopolysaccharide by administering a therapeutically effective amount of nucleic acids containing at least one unmethylated CpG is also provided. The invention also provides a method of modifying the level of a cytokine in a subject having or at risk of having inhaled lipopolysaccharide by administering a therapeutically effective nucleic acid containing at least one unmethylated CpG.

In another embodiment, the invention provides a pharmaceutical composition for treating a subject having or at risk of having an inflammatory response to inhaled lipopolysaccharide including a nucleic acid sequence containing at least one unmethylated CpG in a pharmacologically acceptable carrier.

In a further embodiment, isolated nucleic acid sequences as set forth in SEQ ID NOS:2, 17, 18, 59–65 are provided.

BRIEF DESCRIPTION OF THE DRAWINGS

FIG. 12 is a graph plotting interleukin 4 (IL-4) production pg/ml) in mice over time in response to injection of egg, then SEA (open diamond); egg and CpG ODN, then SEA (open circle); or saline, then saline (open square). The graph shows that the resultant inflammatory response correlates with the levels of the Th2 cytokine IL-4 in the lung.

FIG. 13 is a bar graph plotting interleukin 12 (IL-12) production (pg/ml) in mice over time in response to injection of saline; egg, then SEA; or CpG ODN and egg, then SEA. The graph shows that administration of an oligonucleotide containing an unmethylated CpG motif can actually redirect the cytokine response of the lung to production of IL-12, indicating a Th1 type of immune response.

FIG. 14 is a bar graph plotting interferon gamma (IFN-γ production (pg/ml) in mice over time in response to injection of saline; egg, then saline; or CpG ODN and egg, then SEA. The graph shows that administration of an oligonucleotide containing an unmethylated CpG motif can also redirect the cytokine response of the lung to production of IFN-γ, indicating a Th1 type of immune response.

DESCRIPTION OF THE PREFERRED EMBODIMENTS

Figure 1:
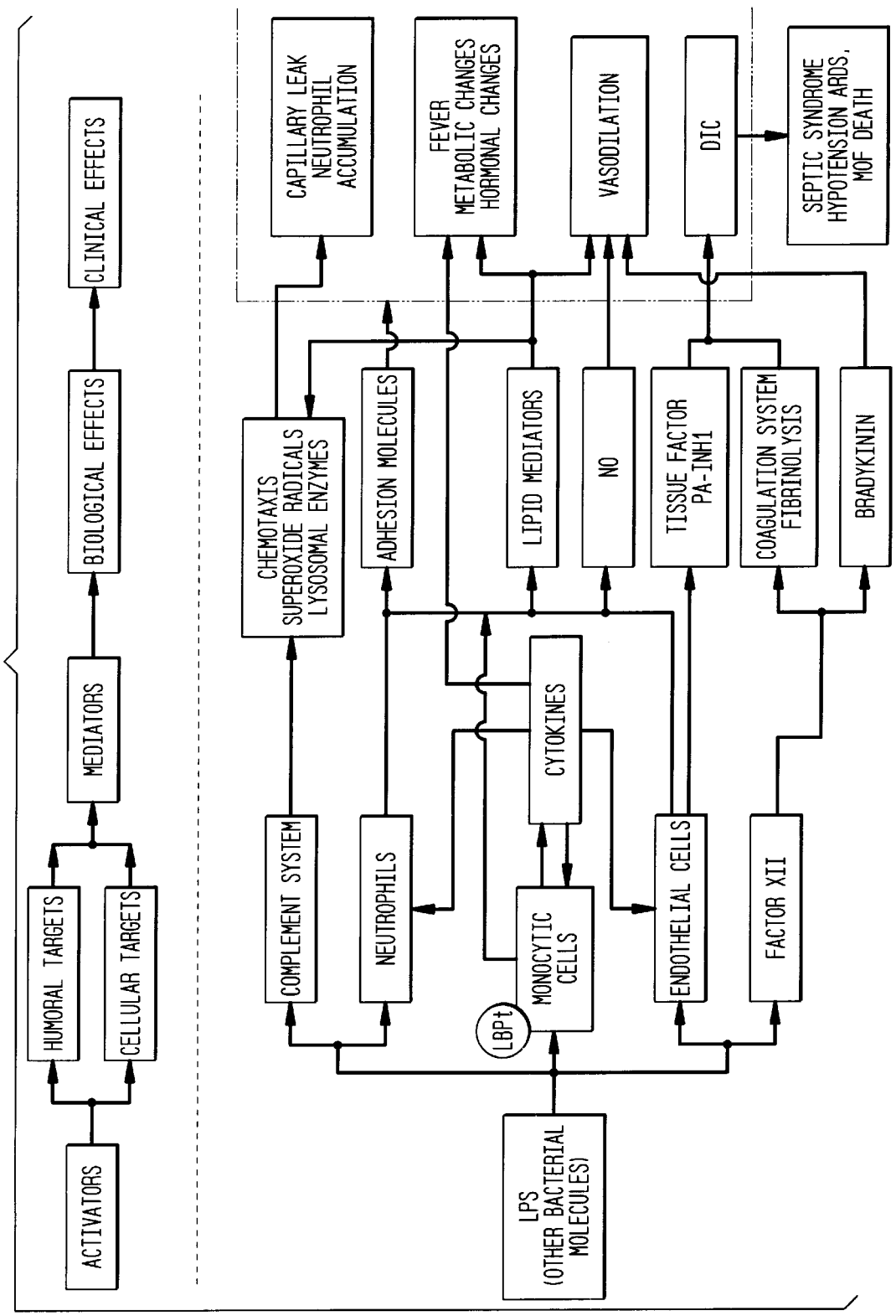
FIG. 1 is a flow chart showing the pathways to sepsis and acute lung injury.

It is to be understood that this invention is not limited to the particular methodology, protocols, sequences, models and reagents described as such may, of course, vary. It is also to be understood that the terminology used herein is for the purpose of describing particular embodiments only, and is not intended to limit the scope of the present invention which will be limited only by the appended claims.

All publications mentioned herein are incorporated herein by reference for the purpose of describing and disclosing the oligonucleotides and methodologies which are described in the publications which might be used in connection with the presently described invention.

The binding of DNA to cells has been shown to be similar to a ligand receptor interaction: binding is saturable, competitive, and leads to DNA endocytosis and degradation into oligonucleotides (Bennet, R. M., et al., *J. Clin. Invest.* 76:2182, 1985). Like DNA, oligodeoxyribonucleotides are able to enter cells in a process which is sequence, temperature, and energy independent (Jaroszewski and Cohen, *Ad. Drug Del. Rev.* 6:235, 1991). An "oligodeoxyribonycleotide" as used herein is a deoxyribonucleic acid sequence from about 3–50 bases in length. Lymphocyte oligodeoxyribonucleotide uptake has been shown to be regulated by cell activation (Krieg, A. M., et al., *Antisense Research and Development* 1:161, 1991). The present invention is based on the finding that certain oligonucleotides (ODN) containing at least one unmethylated cytosine-guanine (CpG) dinucleotide activate the immune response.

In one embodiment, the invention provides a method for treating a subject having or at risk of having an acute decrement in air flow by administering a therapeutically effective amount of a nucleic acid sequence containing at least one unmethylated CpG. The term "nucleic acid" or "oligonucleotide" refers to a polymeric form of nucleotides at least five bases in length. The nucleotides of the invention can be deoxyribonucleotides, ribonucleotides, or modified forms of either nucleotide. Generally, double-stranded molecules are more stable in vivo, while single-stranded molecules have increased activity.

The nucleic acid molecule can include the use of phosphorothioate or phosphorodithioate rather than phosphodiesterase linkages within the backbone of the molecule, or methylphosphorothioate terminal linkages (Krieg, A. M., et al., *Antisense and Nucl Acid Drug Dev* 6:133–9, 1996; Boggs, R. T., et al., *Antisense and Nucl Acid Drug Dev*, 7:461–71, 1997). The phosphate backbone modification can occur at the 5' end of the nucleic acid, for example at the first two nucleotides of the 5' end of the nucleic acid. The phosphate backbone modification may occur at the 3' end of the nucleic acid, for example at the last five nucleotides of the 3' end of the nucleic acid. International Patent Application WO 95/26204, entitled "Inmune stimulation by phosphorothioate oligonucleotide analogs" reports the nonsequence-specific immunostimulatory effect of phosphorothioate modified oligonucleotides. Nontraditional bases such as inosine and queosine, as well as acetyl-, thio- and similarly modified forms of adenine, cytidine, guanine, thymine, and uridine can also be included, which are not as easily recognized by endogenous endonucleases. Other stabilized nucleic acid molecules include: nonionic DNA analogs, such as alky- and aryl-phosphonates (in which the charged oxygen moiety is alkylated). Nucleic acid molecules which contain a diol, such as tetrahyleneglycol or hexaethyleneglycol, at either or both termini are also included. The term "oligonucleotide" includes both single and double-stranded forms of DNA.

A "CpG" or "CpG motif" refers to a nucleic acid having a cytosine followed by a guanine linked by a phosphate bond. The term "methylated CpG" refers to the methylation of the cytosine on the pyrimidine ring, usually occurring the 5-position of the pyrimidine ring. The term "unmethylated CpG" refers to the absence of methylation of the cytosine on the pyrimidine ring. Methylation, partial removal, or removal of an unmethylated CpG motif in an oligonucleotide of the invention is believed to reduce its effect. Methylation or removal of all unmethylated CpG motifs in an oligonucleotide substantially reduces its effect. The effect of methylation or removal of a CpG motif is "substantial" if the effect is similar to that of an oligonucleotide that does not contain a CpG motif.

Preferably the CpG oligonucleotide is in the range of about 8 to 30 bases in size. For use in the instant invention, the nucleic acids can be synthesized de novo using any of a number of procedures well known in the art. For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051–4054, 1986; Froehler et al., *Nucl. Acid. Res.* 14:5399–5407, 1986, ; Garegg et al., *Tet. Let.* 27:4055–4058, 1986, Gaffney et al., *Tet. Let.* 29:2619–2622, 1988). These chemistries can be performed by a variety of automated oligonucleotide synthesizers available in the market. Alternatively, CpG dinucleotides can be produced on a large scale in plasmids, (see Sambrook, T., et al., *Molecular Cloning: A Laboratory Manual*, Cold Spring Harbor laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases.

For use in vivo, nucleic acids are preferably relatively resistant to degradation (e.g., via endo-and exo-nucleases). Secondary structures, such as stem loops, can stabilize nucleic; acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A., *Chem. Rev.* 90:544, 1990; Goodchild, J., *Bioconjugate Chem.* 1:165, 1990).

For administration in vivo, nucleic acids may be associated with a molecule that results in higher affinity binding to target cell (e.g., B-cell, monocytic cell and natural killer (NK) cell) surfaces and/or increased cellular uptake by target cells to form a "nucleic acid delivery complex." Nucleic acids can be ionically or covalently associated with appropriate molecules using techniques which are well known in the art. A variety of coupling or cross-linking agents can be used, e.g., protein A, carbodiimide, and N-succinimidyl-3-(2-pyridyldithio)propionate (SPDP). Nucleic acids can alternatively be encapsulated in liposomes or virosomes using well-known techniques.

In one embodiment, the nucleic acid sequences useful in the methods of the invention are represented by the formula:

 (SEQ ID NO:1)

wherein at least one nucleotide separates consecutive CpGs; $X_1$ is adenine, guanine, or thymidine; $X_2$ is cytosine or thymine, N is any nucleotide and $N_1+N_2$ is from about 0–26 bases. In a preferred embodiment, $N_1$ and $N_2$ do not contain a CCGG quadmer or more than one CGG trimer; and the nucleic acid sequence is from about 8–30 bases in length. However, nucleic acids of any size (even may kb long) can be used in the invention if CpGs are present, as larger nucleic acids are degraded into oligonucleotides inside cells. Preferred synthetic oligonucleotides do not include a CCGG quadmer or more than one CCG or CGG trimer at or near the 5' or 3' terminals and/or the consensus mitogenic CpG motif is not a palindrome. A "palindromic sequence" or "palindrome" means an inverted repeat (i.e., a sequence such as ABCDEE'D'C'B'A', in which A and A' are bases capable of forming the usual Watson-Crick base pairs. An exemplary nucleic acid sequence of the invention is:

 (SEQ ID NO:2).

In another embodiment, the method of the invention includes the use of an oligonucleotide which contains a CpG motif represented by the formula:

 (SEQ ID NO:3)

wherein at least one nucleotide separates consecutive CpGs; $X_1X_2$ is selected from the group consisting of GpT, GpG, GpA, ApT and ApA; $X_3X_4$ is selected from the group consisting of TpT or CpT; N is any nucleotide and $N_1+N_2$ is from about 0–26 bases. In a preferred embodiment, $N_1$ and $N_2$ do not contain a CCGG quadmer or more than one CCG or CGG trimer. CpG ODN are also preferably in the range of 8 to 30 bases in length, but may be of any size (even many kb long) if sufficient motifs are present, since such larger nucleic acids are degraded into oligonucleotides inside of cells. Preferred synthetic oligonucleotides of this formula do not include a CCGG quadmer or more than one CCG or CGG trimer at or near the 5' and/or 3' terminals and/or the consensus mitogenic CpG motif is not a palindrome. Other CpG oligonucleotides can be assayed for efficacy using methods described herein.

A prolonged effect can be obtained using stabilized oligonucleotides, where the oligonucleotide incorporates a phosphate backbone modification (e.g., a phosphorothioate or phosphorodithioate modification). More particularly, the phosphate backbone modification occurs at the 5' end of the nucleic acid for example, at the first two nucleotides of the 5' end of the nucleic acid. Further, the phosphate backbone modification may occur at the 3' end of the nucleic acid for example, at the last five nucleotides of the 3' end of the nucleic acid. Preferred nucleic acids containing an unmethylated CpG have a relatively high stimulation with regard to B cell, monocyte, and/or natural killer cell responses (e.g., induction of cytokines, proliferative responses, lytic responses, among others).

The "stimulation index" is a measure of a CpG ODN to effect an immune response which can be tested in various immune cell assays. The stimulation of the immune response can be assayed by measuring various immune parameters, e.g., measuring the antibody-forming capacity, number of lymphocyte subpopulations, mixed leukocyte response assay, lymphocyte proliferation assay. The stimulation of the immune response can also be measured in an assay to determine resistance to infection or tumor growth. Methods for measuring a stimulation index are well known to one of skill in the art. For example, one assay is the incorporation of $^3$H uridine in a murine B cell culture, which has been contacted with a 20 µM of oligonucleotide for 20 h at 37° C. and has been pulsed with 1 µCi of $^3$H uridine; and harvested and counted 4 h later. The induction of secretion of a particular cytokine can also be used to assess the stimulation index. Without meaning to be bound by theory, for use in vivo, for example to treat a subject having or at risk of having an acute decrement in air flow in response to endotoxin, it is important that the CpG ODN be capable of effectively inducing cytokine secretion by monocytic cells and/or Natural Killer (NK) cell lytic activity. In one method, the stimulation index of the CpG ODN with regard to B-cell proliferation is at least about 5, preferably at least about 10, more preferably at least about 15 and most preferably at least about 20, while recognizing that there are differences in the stimulation index among individuals.

The CpG ODN of the invention stimulate cytokine production (e.g., IL-6, IL-12, IFN-γ, TNF-α and GM-CSF). Exemplary sequences include:

TCCATGTCGCTCCTGATGCT (SEQ ID NO:4),

TCCATGTCGTTCCTGATGCT (SEQ ID NO:5), and

TCGTCGTTTTGTCGTTTTGTCGTT (SEQ ID NO:6).

The CpG ODN of the invention are also useful for stimulating natural killer cell (NK) lytic activity in a subject such as a human. Specific, but nonlimiting examples of such sequences include:

TCGTCGTTGTCGTTGTCGTT (SEQ ID NO:7),

TCGTCGTTTTGTCGTTTTGTCGTT (SEQ ID NO:6),

TCGTCGTTGTCGTTTGTCGTT (SEQ ID NO:8),

GCGTGCGTTGTCGTTGTCGTT (SEQ ID NO:9),

TGTCGTTTGTCGTTTGTCGTT (SEQ ID NO:10),

TGTCGTTGTCGTTGTCGTT (SEQ ID NO:11), and

TCGTCGTCGTCGTT (SEQ ID NO:12).

The nucleic acid sequences of the invention are also useful for stimulating B cell proliferation. Specific, but nonlimiting examples of such sequences include:

TCCTGTCGTTCCTTGTCGTT (SEQ ID NO:13),

TCCTGTCGTTTTTTGTCGTT (SEQ ID NO:14),

TCGTCGCTGTCTGCCCTTCTT (SEQ ID NO:15),

TCGTCGCTGTTGTCGTTTCTT (SEQ ID NO:16),

TCGTCGTTTTGTCGTTTTGTCGTT (SEQ ID NO:6),

TCGTCGTTGTCGTTTGTCGTT (SEQ ID NO:8)

and

TGTCGTTGTCGTTGTCGTT (SEQ ID NO:11).

Preferred CpG ODN can effect at least about 500 pg/ml of TNF-α, 15 pg/ml IFN-γ, 70 pg/ml of GM-CSF 275 pg/ml of IL-6, 200 pg/ml IL-12, depending on the therapeutic indication. These cytokines can be measured by assays well known in the art. The ODNs listed above or other preferred CpG ODN can effect at least about 10%, more preferably at least about 15% and most preferably at least about 20% YAC-1 cell specific lysis or at least about 30%, more preferably at least about 35%, and most preferably at least about 40% 2C11 cell specific lysis, in assays well known in the art (see Example 4).

The term "acute" refers to a condition having a short and relatively severe course. A "decrement in air flow" is a decrease in a measurable parameter of lung function. The terms "lung function" and "pulmonary function" are used interchangeably and shall be interpreted to mean physically measurable operations of a lung including but not limited to inspiratory flow rate, expiratory flow rate, and lung volume. Methods of quantitatively determining pulmonary function are used to measure lung function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e., forced exhalation from maximum inspiration to maximum expiration) is largely technique dependent. In other words, a given patient may produce different FVC values during a sequence of consecutive FVC maneuvers. The FEF 25–75 or forced expiratory flow determined over the midportion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases.

The term "asthma" refers to a disorder of the respiratory system characterized by inflammation, narrowing of the airways and increased reactivity of the airways to inhaled agents. Asthma is frequently, although not exclusively associated with atopic or allergic symptoms.

By "therapeutically effective amount" is meant the quantity of a compound according to the invention necessary to prevent, to cure or at least partially arrest symptoms in a subject. A subject is any mammal, preferably a human. Amounts effective for therapeutic use will, of course, depend on the severity of the disease and the weight and general state of the subject. Typically, dosages used in vitro may provide useful guidance in, the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

An oligonucleotide containing at least one unmethylated CpG can be used alone to activate the immune response or can be administered in combination with another therapeutic modality, either a drug or a surgical procedure. For example, when the oligonucleotide containing at least one unmethylated CpG is administered in conjunction with another therapeutic modality, the oligonucleotide can be administered before, after, and/or simultaneously with the other therapeutic modality. The oligonucleotide containing at least one unmethylated CpG can have an additional efficacy (e.g., through antisense or other means) in addition to its ability to activate the immune response.

In another embodiment, the invention further provides a method of treating a subject having or at risk of having an inflammatory response to LPS by administering to the subject a therapeutically effective amount of a nucleic acid sequence containing at least one unmethylated CpG.

Examples of diseases which can be associated with Gram-negative bacterial infections or endotoxemia include bacterial meningitis, neonatal sepsis, cystic fibrosis, inflammatory bowel disease and liver cirrhosis, Gram-negative pneumonia, Gram-negative abdominal abscess, hemorrhagic shock and disseminated intravascular coagulation. Subjects who are leukopenic or neutropenic, including subjects treated with chemotherapy or immunocompromised subjects (for example with AIDS), are particularly susceptible to bacterial infection and the subsequent effects of endotoxin.

By "lipopolysaccharide" or "LPS" is meant a compound composed of a heteropolysaccharide (which contains somatic O antigen) covalently bound to a phospholipid moiety (lipid a). LPS is a major component of the cell wall of Gram-negative bacteria. By "endotoxin" is meant a heat-stable toxin associated with the outer membranes of certain Gram-negative bacteria, including the enterobacteria, brucellae, neisseriae, and vibrios. Endotoxin, normally released upon disruption of the bacterial cells, is composed of lipopolysaccharide molecules (LPS) and any associated proteins. The phospholipid moiety of LPS, lipid a, is associated with LPS toxicity. When injected in large quantities endotoxin produces hemorrhagic shock and severe diarrhea; smaller amounts cause fever, altered resistance to bacterial infection, leukopenia followed by leukocytosis, and numerous other biologic effects. Endotoxin is a type of "bacterial pyrogen," which is any fever-raising bacterial product. The terms "endotoxin," "LPS," and "lipopolysaccharide" as used herein are essentially synonymous.

The invention further provides a method of treating a subject having or at risk of having an inflammatory response to LPS. It is known that LPS produces an inflammatory response in normal and asthmatic patients. By "inflammatory response" is meant an accumulation of white blood cells, either systemically or locally at the site of inflammation. The inflammatory response may be measured by many methods well known in the art, such as the number of white blood cells (WBC), the number of polymorphonuclear neutophils (PMN), a measure of the degree of PMN activation, such as luminal enhanced-chemiluminescence, or a measure of the amount of cytokines present. The term "cytokine" is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking; place in the extracellular environment. Examples of cytokines include, but are not limited to, TNF-α, IL-10, IL-12, interferon-γ. Importantly, interferon-γ is a key cytokine mediating LPS-induced inflammation (e.g., Ozmen, L., et al., *J. Exp. Med.* 180:907–915, 1994). The release of interferon-γ is induced by IL-12 derived from macrophage/monocyte/dendritic cells. (e.g., Balanchard, D. K., et al., *J. Immunol.* 136:963–970, 1986), and IL-10 inhibits interferon-γ via a macrophage-dependent step in which IL-12 production is inhibited (D'Andrea, a., et al., *J. Exp. Med.* 178:1041–1048, 1993). Without wanting to be bound by theory, it is possible that nucleic acids containing unmethylated CpG could reduce the inflammatory response to LPS by increasing the production and response of IL-10, or by modulating the response of a factor which in turn increase the production and response of IL-10 or IL-6.

The invention further provides a method of modulating the level of a cytokine altered in response to inhaled LPS. The term "modulate" envisions the suppression of expression of a particular cytokine when it is overexpressed, or augmentation of the expression of a particular cytokine when it is underexpressed. Modulation of a particular cytokine can occur locally or systemically. It is believed that the CpG oligonucleotides do not directly activate purified NK cells, but rather render them competent to respond to IL-12 with a marked increase in their IFN-γ production. By inducing IL-12 production and the subsequent increased IFN-γ secretion by NK cells, the immunostimulatory nucleic acids also promote a Th1 type immune response. No direct activation of proliferation or cytokine secretion by highly purified T cells has been found. Cytokine profiles determine T cell regulatory and effector functions in immune responses.

Cytokines also play a role in directing the T cell response. Helper (CD4$^+$) T cells orchestrate the immune response of mammals through production of soluble factors that act on other immune system cells, including other T cells. Most mature CD4$^+$ T helper cells express one of two cytokine profiles: Th1 or Th2. Th1 cells secrete IL-2, IL-3, IFN-γ, TNF-β, GM-CSF and high levels of TNF-α. Th2 cells express IL-3, IL-4, IL-5, IL-6, IL-9, IL-10, IL-13, GM-CSF and low levels of TNF-α. The Th1 subset promotes delayed-type hypersensitivity, cell-mediated immunity, and immunoglobulin class switching to IgG$_{2a}$. The Th2 subset induces humoral immunity by activating B cells, promoting antibody production, and inducing class switching to IgG$_1$ and IgE.

Several factors have been shown to influence commitment to Th1 or Th2 profiles. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear to be required for the establishment of the Th2 cytokine profile and to down-regulate Th1 cytokine production; the effects of IL-4 are in some cases dominant over those of IL-12. IL-13 was shown to inhibit expression of inflammatory cytokines, including IL-12 and TNF-α by LPS-induced monocytes, in a way similar to IL-4. The IL-12 p40 homodimer binds to the IL-12 receptor and antagonizes IL-12 biological activity; thus it blocks the pro-Th1 effects of IL-12.

The invention may be used to treat individuals who are "at risk" of developing a acute decrement in airflow or who are at risk of LPS exposure. These individuals may be identified by any diagnostic means, or by epidemiological evidence such as exposure data. These individuals may be treated by a method of the invention prior to, at the time of, or after the actual onset of the clinical appearance. The "clinical appearance" can be any sign or symptom of the disorder.

This invention further provides administering to a subject having or at risk of having an inflammatory response to inhaled LPS, a therapeutically effective dose of a pharmaceutical composition containing the compounds of the present invention and a pharmaceutically acceptable carrier. "Administering" the pharmaceutical composition of the present invention may be accomplished by any means known to the skilled artisan.

The pharmaceutical compositions according to the invention are in general administered topically, intravenously, orally, parenterally or as implants, and even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, Science 249:1527–1533, 1990, which is incorporated herein by reference.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Methods for Pulmonary Response to Inhaled LPS

In the first series of experiments, mice were intravenously treated with 20 base pair (bp) oligonucleotides containing CpG motifs (CpG oligo) or 20 bp oligonucleotides without embedded CpG motifs (non CpG oligo) 30 min, 4 hours, or 12 hours prior to a 4 hour inhalation challenge with *E. coli* LPS (1.5 $\mu g/m^3$). To determine whether unmethylated CpG motifs were responsible for the protective effect, we pretreated mice with oligonucleotides containing either unmethylated CpG motifs or methylated CpG motifs prior to an inhalation challenge with *E. coli* LPS. Finally, to determine the role of IL-10, we pretreated IL-10 knockout mice with CpG oligos and then performed a similar inhalation challenge with *E. coli* LPS. Immediately post inhalation challenge, all mice were sacrificed, blood samples were obtained, whole lung lavage was performed, and lungs were harvested for mRNA analysis.

Animals. C3H/HeBFEJ, C57BL/6, and C57BL/6-Il10$^{tm1Cgn}$ male mice (Jackson Laboratories, Bar Harbor, Me.) were obtained at 6 weeks of age and used within 2 weeks. All animal care and housing requirements set forth by the National Institutes of Health Committee on Care and Use of Laboratory Animals of the Institute of Laboratory Animal Resources were followed, and animal protocols were reviewed and approved by the Institutional Animal Care and Use Committee. Mice were maintained in woodchip bedding (Northeastern Product, Warrensberg, N.Y.), with food (Formulab Chow 5008, PMI, Richmond, Ind.) and water supplied ad libitum.

Oligonucleotides. Twenty base pair oligonucleotides were synthesized with and without the embedded CpG motifs (Oligos etc., Wilsonville, Oreg.). These oligonucleotides contained a nuclease-resistant phosphorothioate-modified backbone, and were purified by two rounds of ethanol precipitation prior to use. The CpG dinucleotide was flanked by two 5' purines and two 3' pyrimidines to enhance the stimulatory effect of the oligonucleotide.

The "nonstimulatory" oligonucleotide was identical to the stimulatory oligonucleotide except that the two embedded CpG motifs were modified, one appearing as an ApG motif and the other appearing as a GpC motif. The two synthesized oligonucleotides had the following sequences:

CpG Oligonucleotide: ATAAT<u>CG</u>A<u>CG</u>TTCAAGCAAG (SEQ ID NO:2)

Non-CpG oligonucleotide: ATAAT<u>A</u>G<u>A</u><u>GC</u>TTCAAGCAAG (SEQ ID NO:18)

Methylation Protocol. DNA was methylated as we have described previously (Krieg, A. M., et al., *Nature* 374:546–9, 1995) with 2 U CpG methylase (New England Biolabs; Beverly, Mass.) per µg DNA for 18 hours at 37° C. Methylated DNA was tested to confirm that it was completely protected against digestion with Hpa-II but not Msp-I.

Chemicals. Endotoxin was purchased as lyopholized purified *E. coli* 0111:B4 lipopolysaccharide (LPS) (Sigma Chemical Co., St. Louis, Mo., PN# L2630) and had a specified activity of $1.3 \times 10^6$ ng/mg and protein content less than 3%.

Endotoxin Assay. The endotoxin concentrations of LPS solution, LPS aerosol, and oligonucleotides were assayed using the chromogenic Limulus amebocyte lysate (LAL) assay (QCL-1000, Whittaker Bioproducts, Inc., Walkersville, Md.) with sterile, pyrogen-free labware and a temperature controlled microplate block and microplate reader (405 nm). The LPS solution was serially diluted in pyrogen-free water and assayed. The airborne concentration of LPS was assessed by sampling 0.30 m$^3$ of air drawn from the exposure chamber through 47 mm binder-free glass microfiber filters (EPM-2000, Whatman Intl. Ltd., Maidstone, England) held within a 47 mm stainless steel in-line air sampling filter holder (Gelman Sciences Inc., Ann Arbor, Mich.). Air sampling filters were extracted with 10 ml of pfw at room temperature with gentle shaking for 1 hour. They were then serially diluted with pfw and assayed for endotoxin. Four to 6 air samples were assayed for each exposure. All standard curves (0.1 to 1.0 EU/ml) achieved a linear regression coefficient exceeding r=0.995. Spiked samples and filter blanks and participates were run routinely; interlaboratory validation studies were also performed routinely.

Exposure Protocol and Monitoring Equipment. LPS aerosols were generated into a glass 20 L exposure chamber using a PITT#1 nebulizer supplied with extract by a syringe pump. Liquid feed rates ranged from 0.0027 to 0.21 ml/min. HEPA-filtered air was supplied to the nebulizer at flow rates ranging from 10 to 17 L/min. Mixing within the chamber was aided by a magnetically coupled rotor. The chamber atmosphere was exchanged at 1 change/min. LPS concentrations were determined by sampling the total chamber outflow. Particle size distributions were determined with an Aerodynamic Particle Sizer (TSI, Inc., St. Paul, Minn.) and gravimetrically with a Marble personal cascade impactor and Mylar media (Thorne, P. S., *Am. J. Ind. Med.* 25:109–112, 1997) by sampling within the exposure chamber.

Lung Lavage. Immediately following the inhalation challenge, mice were euthanized, the chest was opened, and lungs were lavaged in situ via PE-90 tubing inserted into the exposed trachea. A pressure of 25 cm H$_2$O was used to wash the lungs with 6.0 ml of sterile pyrogen free saline. Following whole lung lavage, the lungs were isolated and frozen in liquid nitrogen and stored at −70° C.

Treatment of Bronchoalveolar Lavage Fluid. A standard method (Schwartz, D. A., et al., *Am. J. Physiol.* 267:L609–617, 1994) of processing the sample was as follows: immediately following lavage, the volume was noted and 15 ml conical tubes were centrifuged for 5 min at 200×g. The supernatant fluid was decanted and frozen at −70° C. for subsequent use. The residual pellet of cells was resuspended and washed twice in HBSS (without Ca$^{++}$ or Mg$^{++}$). After the second wash, a small aliquot of the sample was taken for cell count using a hemocytometer. The cells were then washed once more and resuspended in RPMI medium so that the final concentration gave a cell count of $1 \times 10^6$ cells/ml. The cells which were present in 10–12 µl of the $1 \times 10^6$ ml cell suspension were spun for 5 minutes onto a glass slide using a special filter card using a cytocentrifuge (Cytospin-2; Shanden Southern, Sewickley, Pa.). Staining was carried out using a Diff Quick Stain Set (Harleco, Gibbstown, N.Y.). The slide was then dried, one drop of optically clear immersion oil was put on the slide over the cells and a coverslip was placed on top.

Cytokine Analysis of lavage fluid and serum. Lavage fluid was assayed for TNF-α, MIP-2, IL-6, IL-10, IL-12, and IFN-γ. In all cases, a polyclonal antibody specific for the murine recombinant cytokine (TNF-α, MIP-2, IL-6, IL-10, IL-12, or IFN-γ) was used as a capture reagent in a standard commercially available sandwich ELISA (R & D Systems; Minneapolis, Minn.). The limit for detection for TNF-α is 5.1 pg/ml, MIP-2 is 1.5 pg/ml, IL-6 is 10 pg/ml, IL-10 is 10 pg/ml, IL-12 is 5 pg/ml, and IFN-γ is 10 pg/ml.

Preparation of RNA and Multi robe RNase Protection Assay. Total RNA was extracted from lung specimens using the single-step method (Chomczynski and Pandsacchi, *Anal Biochem* 162:156–9, 1987; Kedzierski, W., *Biotechniques* 10:210–214,1991), lysing flash frozen lung in RNA STAT-60 (Tel-Test B; Friendswood, Tex.). The composition of RNA STAT-60 includes phenol and guanidinium thiocyanate in a monophase solution. The lung parenchyma was homogenized in the RNA STAT-60 using a polytron homogenizer. Chloroform was added, the total RNA was precipitated from the aqueous phase by addition of isopropanol, and the total RNA was washed with ethanol and solubilized in water. After drying the pellet in a vacuum desiccator, the yield and purity of RNA was quantitated by measuring the ratio of absorbances at 260 and 280 nm. Mini-gel electrophoresis was used to confirm the integrity of the 28s and 18s rRNA bands. Gene transcripts were detected using the RNase protection assay as previously described (Hobbs, J. M., et al., *J. Immunol.* 150:3602, 1993). Equivalent amounts of RNA were examined, as judged by the amount of L32, which encodes an ubiquitously expressed ribosome subunit protein (Rajchel, A., et al., *Nucl. Acid. Res.* 16:2347, 1987) in each sample. Commercially available probes were used to detect TNF-α, MIP-2, IL-6, IL-10, IL-12, and IFN-γ.

Statistical Analysis. Three comparisons were pursued in this analysis: 1) the effect of intravenous CpG containing oligonucleotides versus oligonucleotides without embedded CpG motifs in modulating the inflammatory response to inhaled LPS; 2) the effect of unmethylated CpG motifs versus methylated CpG motifs in controlling the inflammatory response to LPS; and 3) the role of IL-10 in mediating the protective effect of unmethylated CpG containing oligonucleotides. The inflammatory response was assessed using lavage cellularity, lavage fluid cytokine concentration, serum concentration of cytokines, and the relative concentration of mRNA for specific cytokines in the lung parenchyma. After making sure that the data were normally distributed, statistical comparisons were made using parametric statistics including the Student's T-test (Rosner, R., *Fundamentals of Biostatistics* (3rd edition) Boston, Mass., PWS-Kent, 1980).

EXAMPLE 2

CpG ODN Reduces the Pulmonary Response to Inhaled LPS and Stimulates the Immune Response Pretreatment with CpG oligonucleotides (ODN) resulted in a systemic inflammatory response. Although intravenous treatment with CpG ODN did not affect the concentration of peripheral white blood cells; compared to non-CpG ODN, treatment with CpG ODN prior to LPS inhalation resulted in a higher concentration of PMNs 30 min, 4 hours, and 12 hours after injection. As expected, intravenous treatment with CpG oligonucleotides also affected the concentration of cytokines in the serum.

Figure 2:
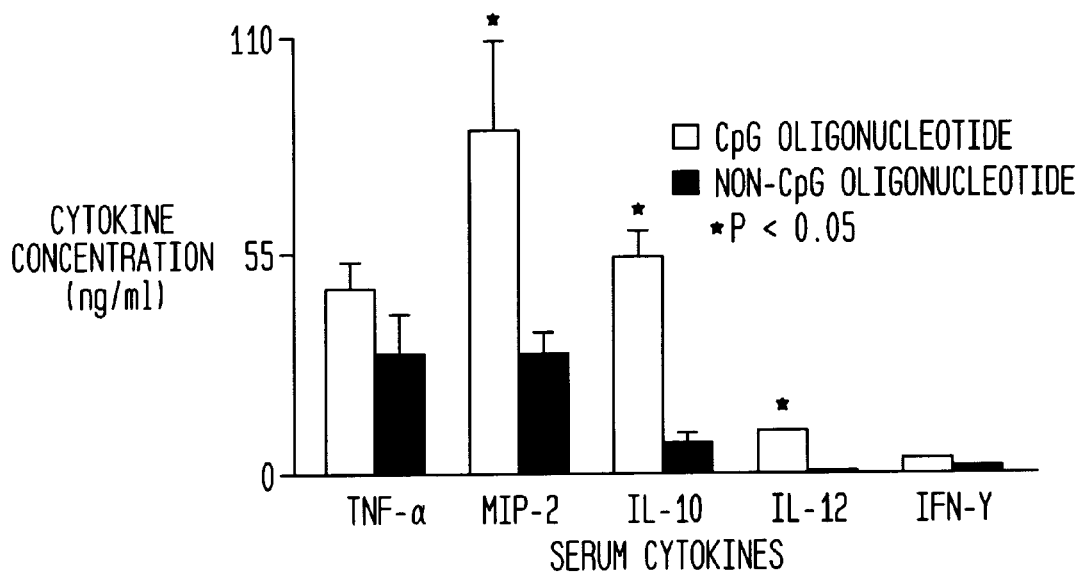
FIG. 2 is a graph plotting the concentration of cytokines (TNF-α, MIP-2, IL-10, IL-12, and IFN-γ) in the serum four hours after intravenous treatment with either an oligonucleotide containing embedded CpG motifs or an oligonucleotide without CpG motifs. Serum samples were obtained immediately following an inhalation challenge with *E. coli* LPS. Error bars show Standard Error (SE).

Compared to non-CpG ODN, CpG ODN resulted in an increase in the concentration of MIP-2, IL-10, and IL-12 in the serum of mice following LPS inhalation (FIG. 2). These differences were most pronounced 30 min and 4 hours after intravenous administration but were still present 12 hours after exposure to CpG containing oligonucleotides. No differences were observed for the serum concentration of TNF-α, IL-6, and IFN-γ at any of the time points in mice pre-treated with either oligonucleotide and then exposed to LPS (data not shown for IL-6).

Figure 3:
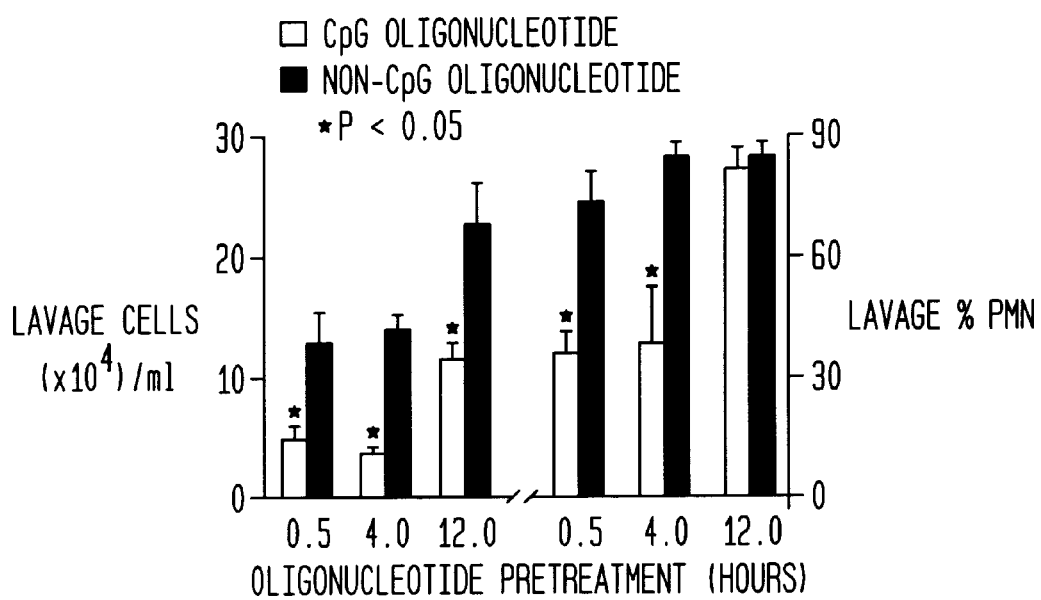
FIG. 3 is a graph plotting the concentration of total cells and PMNs in the whole lung lavage fluid following inhalation challenge with *Escherichia coli* LPS. Thirty minutes, four hours and 12 hours prior to the inhalation challenge, mice were either treated with an oligonucleotide containing embedded CpG motifs or were treated with an oligonucleotide without CpG motifs. Error bars show SE.
Figure 4:
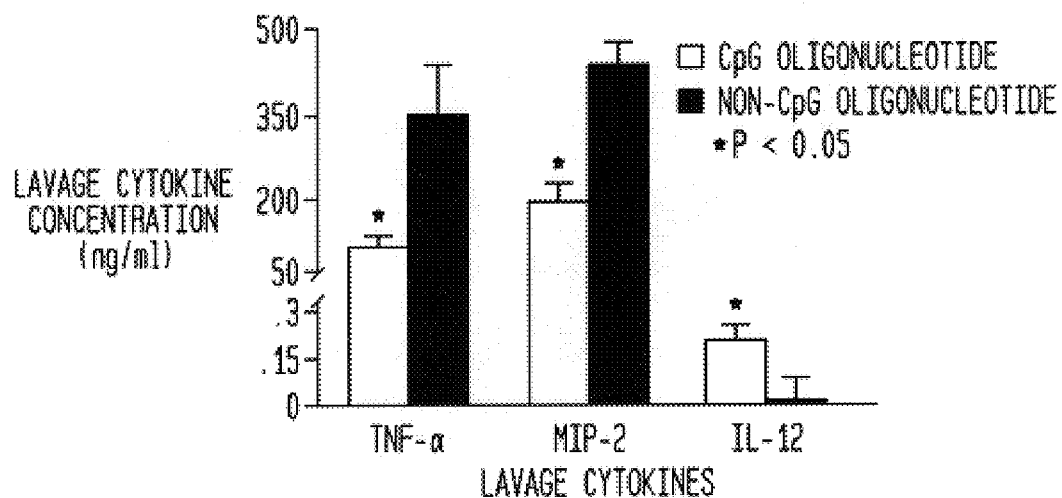
FIG. 4 is a graph showing the concentration of cytokines (TNF-α, MIP-2, and IL-12) in the whole lung lavage fluid following inhalation of *E. coli* LPS. Mice were pretreated with an oligonucleotide containing embedded CpG motifs or were pretreated with an oligonucleotide without CpG motifs four hours prior to inhalation challenge with LPS. Error bars show SE.
Figure 5:
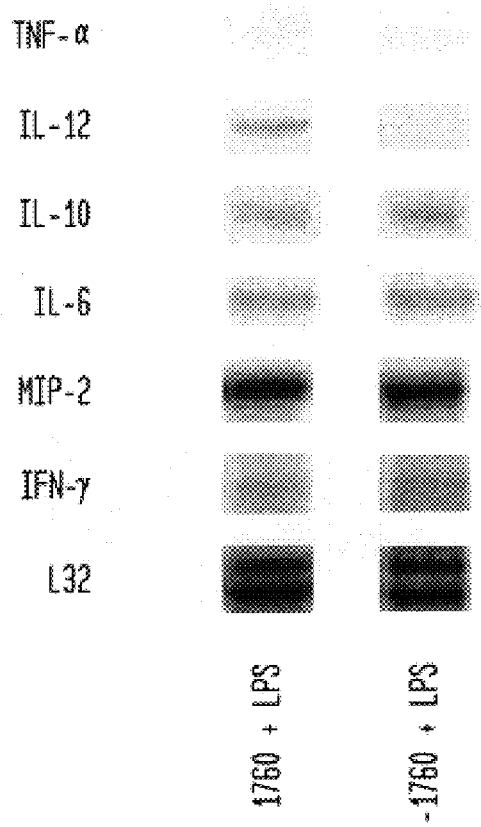
FIG. 5 is an autoradiograph showing an RNase protection assay of the total mRNA isolated from lungs of mice exposed to *E. coli* LPS by inhalation. Mice were pretreated with an oligonucleotide containing embedded CpG motifs or were pretreated with an oligonucleotide without CpG motifs four hours prior to inhalation challenge with LPS. L32 encodes a ribosomal protein and was used to assess the concentration of RNA loaded onto the gel.

Pretreatment with CpG containing oligonucleotides reduced the pulmonary response to inhaled LPS. Animals pretreated with CpG oligonucleotides at 0.5, 4, and 12 hours had a reduced concentration of cells in the lavage fluid following inhalation challenge with LPS (FIG. 3). However, this effect appeared to be time dependent since pretreatment with oligonucleotide at 0.5 and 4 hours resulted in a reduced percentage of lavage PMNs while pretreatment with the oligonucleotide 12 hours prior to the inhalation challenge did not affect the percentage of lavage PMNs (FIG. 3). Although pretreatment with CpG containing oligonucleotides resulted in significant changes in the concentration of cytokines in the lavage fluid, the changes in cytokine concentration were predominantly evident when mice were pretreated with CpG oligonucleotides 4 hours prior to the inhalation challenge. While significant reductions were observed in the concentration of TNF-α and MIP-2, the lavage fluid concentration of IL-12 was elevated following treatment with CpG oligonucleotides 4 hours prior to the inhalation challenge (FIG. 4). IL-6, IL-10, and IFN-γ were not measurable in the lavage fluid following inhalation of LPS at any of the time points. Interestingly, results from the RNase protection assay indicate that total lung mRNA concentrations for TNF-α, MIP-2, IL-6, IL-10, and IFN-γ are similar in mice pretreated with the CpG and non-CpG containing oligonucleotide (FIG. 5). These results also demonstrate that mRNA IL-12 appears to be upregulated in the lung only from mice pretreated with CpG containing oligonucleotides.

Figure 6:
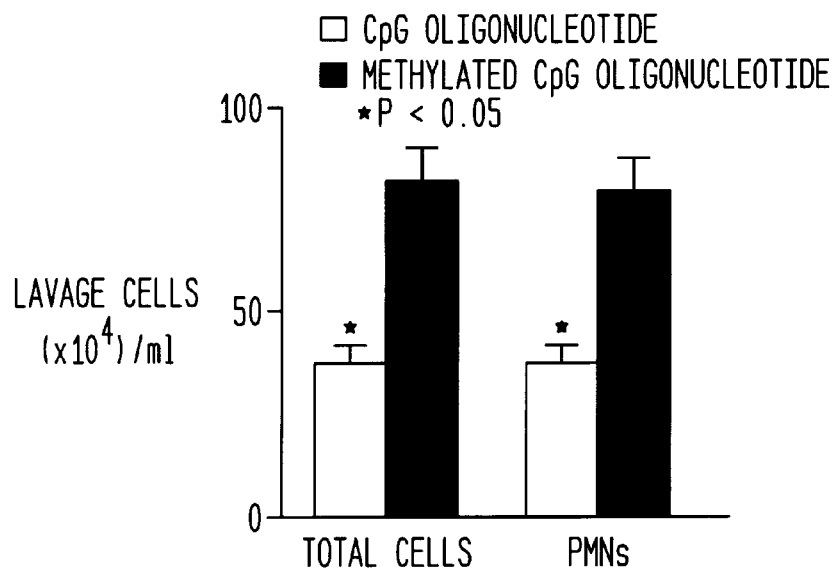
FIG. 6 is a graph plotting the concentration of total cells and PMNs in the whole lung lavage fluid following inhalation of *E. coli* LPS. Mice were pretreated with an oligonucleotide containing embedded CpG motifs or were pretreated with an oligonucleotide without CpG motifs four hours prior to inhalation challenge with LPS. Error bars show SE.

To determine the specificity of the CpG oligonucleotides in suppressing the inflammatory response to inhaled LPS, the CpG motifs were methylated. The immunosuppressive effects of two identical oligonucleotides, one with unmethylated CpG motifs and the other with methylated CpG motifs, were compared. Methylating the CpG motifs abolished the protective effect of CpG oligonucleotides in preventing the cellular inflammatory response to inhaled LPS (FIG. 6).

Further experiments were conducted with the following oligonucleotides:

| | |
|---|---|
| 1908 | ATAATAGAGCTTCAAGCAAG (SEQ ID NO:18) |
| 1760 | ATAATCGACGTTCAAGCAAG (SEQ ID NO:2) |
| 1631 | CGCGCGCGCGCGCGCGCGCG (SEQ ID NO:59) |
| 1835 | TCTCCCAGCGAGCGCCAT (SEQ ID NO:60) |
| 1759 | ATAATCCAGCTTGAACCAAG (SEQ ID NO:61) |
| 1826 | TCCATGACGTTCCTGACGTT (SEQ ID NO:62) |
| 1585 | GGGGTCAACGTTGAGGGGGG (SEQ ID NO:63) |
| 2010 | GCGGCGGGCGGCGCGCGCCC (SEQ ID NO:54) |
| 1972 | GGGGTCTGTGCTTTTGGGGGG (SEQ ID NO:64) |
| 2001 | GGCGGCGGCGGCGGCGGCGG (SEQ ID NO:65) |

Mice were pretreated with the indicated oligonucleotide and then challenged through the airways with LPS as described above. A saline challenge was used as a control. The lungs of the mice were lavaged, and the number of cell per ml, number of polymorphonuclear cells (PMN) per ml, and the percentage of polymorphonuclear cells in the airways was determined (see Table 1).

TABLE 1

| ODN Number | cells/ml × $10^4$ | PMN/ml × $10^5$ | % PMN |
|---|---|---|---|
| expt 1, C3H/BFeJ mice | | | |
| 1908 | 61.4 ± 15.9 | 59.2 ± 15.7 | 95.8 ± 0.95 |
| 1760 | 27.8 ± 3.5* | 25.8 ± 3.0* | 93.3 ± 2.3 |
| 1631 | 47.6 ± 11.1 | 46.1 ± 10.7 | 96.8 ± 1.11 |
| 1835 | 43.8 ± 7.1 | 44.4 ± 7.1 | 96.8 ± 0.75 |
| 1759 | 71.0 ± 19.8 | 67.7 ± 20.4 | 96.8 ± 2.6 |
| 1826 | 39.8 ± 7.8 | 38.3 ± 7.9 | 93.5 ± 1.4 |
| None (saline) | 71.0 ± 7.4 | 69.3 ± 6.9 | 97.8 ± 1.3 |
| expt 2, C57 Bl/6 mice | | | |
| 1908 | 18.0 ± 2.6 | 16.6 ± 2.7 | 91.2 ± 3.7 |
| 1760 | 10.2 ± 2.3* | 8.6 ± 2.1* | 82.0 ± 3.0 |
| 1585 | 11.0 ± 2.2* | 9.5 ± 2.2* | 84.6 ± 2.9 |
| 2010 | 14.1 ± 2.1 | 11.8 ± 1.9 | 83.4 ± 2.1 |
| None (saline) | 17.9 ± 3.4 | 16.9 ± 2.1 | |
| expt 3 | | | |
| 1908 | 19.0 ± 2.5 | 16.9 ± 2.1 | 89.4 ± 1.4 |
| 1760 | 9.1 ± 0.8* | 7.7 ± 0.7* | 84.6 ± 0.5 |
| 1972 | 15.3 ± 1.6 | 13.5 ± 1.4 | 84.2 ± 1.2 |
| 2001 | 13.0 ± 1.6* | 11.8 ± 1.6 | 90.4 ± 2.2 |

*$P>0.05$, Mann-Whitney U test

In experiment 1, both oligonucleotide 1760 and 1826 appear to be effective. In experiment 2, oligonucleotide 1760 and 1585 were effective. Oligonucleotide 2010 also appears to have had a modest effect. In experiment 3, oligonucleotide 1760 was effective. A modest effect was seen with oligonucleotide 2001. Thus the best oligonucleotides for inducing a therapeutic effect fit the motifs shown in SEQ ID NO:1 and SEQ ID NO:3. Oligonucleotides such as 2001 and 2010, which contain CpG motifs with CCGG, CCG, and CGG, can also have a beneficial effect.

The results indicate that CpG containing oligonucleotides substantially reduce the inflammatory response to inhaled LPS and that the protective effect appears to be specific to unmethylated CpG motifs embedded within the oligonucleotide. These findings suggest that oligonucleotides containing CpG motifs may prove helpful in controlling the inflammatory response to inhaled LPS and other environmental agents.

EXAMPLE 3

The Role of IL-10

Figure 7:
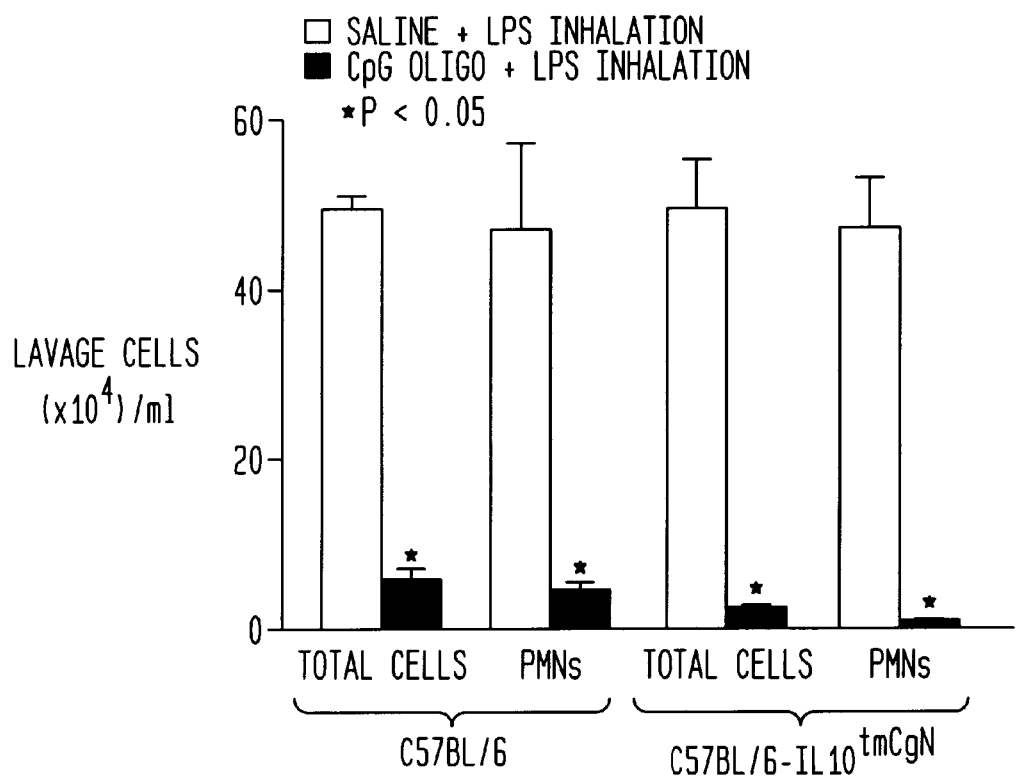
FIG. 7 is a graph showing the concentration of total cells and PMNs in the whole lung lavage fluid following inhalation of *E. coli* LPS. C57BL/6 mice and IL-10 knockout mice (C57BL/6-IL10$^{tm1Cgn}$) were pretreated with either an oligonucleotide containing embedded CpG motifs or with intravenous saline four hours prior to inhalation challenge with LPS. Error bars show SE.

Since endogenous and exogenous IL-10 are known to suppress the inflammatory response to LPS (Cassatella, M. A., et al., *J. Exp. Med.* 178:2207, 1993; Berg, D. J., et al., *J. Clin. Invest.* 96:2339–2347, 1995), IL-10 might play a critical role in mediating the immunosuppressive effects of CpG oligonucleotides. To pursue this hypothesis, IL-10 knockout (C57BL/6-Il10$^{tm1Cgn}$) mice and C57BL/6 control mice were pretreated with CpG containing oligonucleotides and then an inhalation challenge with *E. coli* LPS was performed. Compared to pretreatment with intravenous saline, CpG containing oligonucleotides significantly reduced the total cellularity and the concentration of PMNs in the lavage fluid in both C57BL/6 and mice with a disrupted IL1-10 gene (C57BL/6-Il10$^{tm1Cgn}$) (FIG. 7). Importantly, the immunosuppressive effects of CpG oligonucleotides were equally effective in mice with a disrupted IL-10 gene compared to wild type mice.

The results indicate that the protective effect of unmethylated CpG motifs is not dependent on IL-10.

EXAMPLE 4

Induction of NK Activity

Phosphodiester ODN were purchased from Operon Technologies (Alameda, Calif.). Phosphorothioate ODN were purchased from the DNA core facility, University of Iowa, or from The Midland Certified Reagent Company (Midland Tex.). *E. coli* (strain B) DNA and calf thymus DNA were purchased from Sigma (St. Louis, Mo.). All DNA and ODN were purified by extraction with phenol:chloroform:isoamyl alcohol (25:24:1) and/or ethanol precipitation. The LPS level in ODN was less than 12.5 ng/mg and *E. coli* and calf thymus DNA contained less than 2.5 ng of LPS/mg of DNA by Limulus assay.

Virus-free, 4–6 week old, DBA/2, C57BL/6 (B6) and congenitally athymic BALB/C mice were obtained on contract through the Veterans Affairs from the National Cancer Institute (Bethesda, Md.). C57BL/6 SCID mice were bred in the SPF barrier facility at the University of Iowa Animal Care Unit.

Human peripheral blood mononuclear leukocytes (PBMC) were obtained as previously described (e.g., Ballas, Z. K. et al., *J. Allergy Clin. Immunol.* 85:453, 1990). Human or murine cells were cultured at 5×10$^6$/well, at 37° C. in a 5% $CO_2$ humidified atmosphere in 24-well plates with medium alone or with CpG or non-CpG ODN at the indicated concentrations, or with *E. coli* or calf thymus (50 μg/ml) at 37° C. for 24 hr. All cultures were harvested at 18 hr. and the cells were used as effectors in a standard 4 hr. $^{51}$Cr-release assay against K562 (human) or YAC-1 (mouse) target cells as previously described. For calculation of lytic units (LU), 1 LU was defined as the number of cells needed to effect 30% specific lysis. Where indicated, neutralizing antibodies against IFN-γ (Lee Biomolecular, San Diego, Calif.) or IL-12 (Pharmingen) or their isotype controls were added at the initiation of cultures to a concentration of 10 μg/ml. For anti-IL-12 addition, 10 μg of each of the 4 MAB (or isotype controls) were added simultaneously. Recombinant human IL-2 was used at a concentration of 100 U/ml.

Experiments were conducted to determine whether CpG containing oligonucleotides stimulated the activity of natural killer (NK) cells in addition to B cells. As shown in Table 2, a marked induction of NK activity among mouse spleen cells cultured with CpG ODN 1: GCTAGACGTTAGCGT (SEQ ID NO:19) and 3Dd: GAGAAXGCTGGACCTTCCAT (SEQ ID NO:20), (where X=5 methyl cytosine) was observed. In contrast, there was relatively no induction in effectors that had been treated with non-CpG control ODN.

TABLE 2

Induction Of NK Activity By CpG Oligodeoxynucleotides (ODN)

|  | % YAC-1 Specific Lysis* Effector: Target | | % 2C11 Specific Lysis Effector: Target | |
| --- | --- | --- | --- | --- |
| ODN | 50:1 | 100:1 | 50:1 | 100:1 |
| None | −1.1 | −1.4 | 15.3 | 16.6 |
| 1 | 16.1 | 24.5 | 38.7 | 47.2 |
| 3Dd | 17.1 | 27.0 | 37.0 | 40.0 |
| non-CpG ODN | −1.6 | −1.7 | 14.8 | 15.4 |

Induction of NK activity by DNA containing CpG motifs, but not by non-CpG DNA.

Bacterial DNA cultured for 18 hrs. at 37° C. and then assayed for killing of K562 (human) or Yac-1 (mouse) target cells induced NK lytic activity in both mouse spleen cells depleted of B cells, and human PBMC, but vertebrate DNA did not (Table 3). To determine whether the stimulatory activity of bacterial DNA may be a consequence of its increased level of unmethylated CpG dinucleotides, the activating properties of more than 50 synthetic ODN containing unmethylated, methylated, or no CpG dinucleotides was tested. The results, summarized in Table 3, demonstrate that synthetic ODN can stimulate significant NK activity, as long as they contain at least one unmethylated CpG dinucleotide (Ballas, Z., et al., *J. Immunol* 157:1840–1845, 1996). No difference was observed in the stimulatory effects of ODN in which the CpG was within a palindrome (such as ODN 1585, which contains the palindrome AACGTT) from those ODN without palindromes (such as 1613 or 1619), with the caveat that optimal stimulation was generally seen with ODN in which the CpG was flanked by two 5' purines or a 5' GpT dinucleotide and two 3' pyrimidines. Kinetic experiments demonstrated that NK activity peaked around 18 hrs. after addition of the ODN. The data indicates that the murine NK response is dependent on the prior activation of monocytes by CpG DNA, leading to the production of IL-12, TNF-α, and IFN.

TABLE 3

Induction of NK Activity by DNA Containing CpG Motifs but not by Non-CpG DNA

|  | DNA or Cytokine Added Human Cells |  | Mouse | LU/10⁶ Cells |
|---|---|---|---|---|
| Expt. 1 | None |  | 0.00 | 0.00 |
|  | IL-2 |  | 16.68 | 15.82 |
|  | E. Coli DNA |  | 7.23 | 5.05 |
|  | Calf thymus DNA |  | 0.00 | 0.00 |
| Expt. 2 | None |  | 0.00 | 3.28 |
|  | 1585 ggGGTCAA<u>CG</u>TTGACgggg | (SEQ ID NO:21) | 7.38 | 17.98 |
|  | 1629 --------gtc-------- | (SEQ ID NO:22) | 0.00 | 4.4 |
| Expt. 3 | None |  | 0.00 |  |
|  | 1613 GCTAGA<u>CG</u>TTAGTGT | (SEQ ID NO:23) | 5.22 |  |
|  | 1769 -------X----- | (SEQ ID NO:24) | 0.02 | ND |
|  | 1619 TCCATGT<u>CG</u>TTCCTGATGCT | (SEQ ID NO:5) | 3.35 |  |
|  | 1765 --------X----------- | (SEQ ID NO:25) | 0.11 |  |

CpG dinucleotides in ODN sequences are indicated by underlining; X indicates methylcytosine. Lower case letters indicate nuclease resistant phosphorothioate modified internucleotide linkages which, in titration experiments, were more than 20 times as potent as non-modified ODN, depending on the flanking bases. Poly G ends (g) were used in some ODN, because they significantly increase the level of ODN uptake. Dashes indicate some bases are identical to those in the directly preceding sequence, with the exception of changes noted.

Immune activation by CpG motifs may depend on bases flanking the CpG, and the number and spacing of the CpGs present within an ODN. Although a single CpG in an ideal base context can be a very strong and useful immune activator, superior effects can be seen with ODN containing several CpGs with the appropriate spacing and flanking bases. For activation of murine B cells, the optimal CpG motif is TGACGTT.

The following studies were conducted to identify optimal ODN sequences for stimulation of human cells by examining the effects of changing the number, spacing, and flanking bases of CpG dinucleotides.

Identification of phosphorothioate ODN with optimal CpG motifs for activation of human NK cells To have clinical utility, ODN must be administered to a subject in a form that protects them against nuclease degradation. Methods to accomplish this with phosphodiester ODN are well known in the art and include encapsulation in lipids or delivery systems such as nanoparticles. This protection can also be achieved using chemical substitutions to the DNA such as modified DNA backbones including those in which the internucleotide linkages are nuclease resistant. Some modifications may confer additional desirable properties such as increasing cellular uptake. For example, the phosphodiester linkage can be modified via replacement of one of the nonbridging oxygen atoms with a sulfur, which constitutes phosphorothioate DNA. Phosphorothioate ODN have enhanced cellular uptake (Krieg et al., *Antisense Res. Dev.* 6:133, 1996) and improved B cell stimulation if they also have a CpG motif. Since NK activation correlates strongly with in vivo adjuvant effects, the identification of phosphorothioate ODN that will activate human NK cells is very important.

The effects of different phosphorothioate ODNs, which contain CpG dinucleotides in various base contexts, on human NK activation (Table 4) were examined. ODN 1840, which contained 2 copies of the TGTCGTT (SEQ ID NO:17 motif, had significant NK lytic activity (Table 4). To further identify additional ODNs optimal for NK activation, approximately one hundred ODN containing different numbers and spacing of CpG motifs, were tested with ODN 1982 serving as a control. Sample results are shown in Table 5.

Effective ODNs generally began with a TC or TG at the 5' end, however, this requirement was not mandatory. ODNs with internal CpG motifs (e.g., ODN 1840) are generally less potent stimulators than those in which a GTCGCT (SEQ ID NO:49) motif immediately follows the 5' TC (e.g., ODN 1967 and 1968). ODN 1968, which has a second GTCGTT (SEQ ID NO:49) motif in its 3' half, was consistently more stimulatory than ODN 1967, which lacks this second motif ODN 1967, however, was slightly more potent than ODN 1968 in experiments 1 and 3, but not in experiment 2. ODN 2005, which has a third GTCGTT (SEQ ID NO:49) motif, induced slightly higher NK activity on average than 1968. However, ODN 2006, in which the spacing between the GTCGTT (SEQ ID NO:49) motifs was increased by the addition of two Ts between each motif, was slightly superior to ODN 2005 and to ODN 2007, in which only one of the motifs had the addition of the spacing two Ts. The minimal acceptable spacing between CpG motifs is one nucleotide as long as the ODN has two pyrimidines preferably T) at the 3' end (e.g., ODN 2015). Surprisingly, joining two GTCGTT (SEQ ID NO:49) motifs end to end with a 5' T also created a reasonably strong inducer of NK activity (e.g., ODN 2016). The choice of thymine (T) separating consecutive CpG dinucleotides is not absolute, since ODN 2002 induced appreciable NK activation despite the fact that adenine (a) separated its CpGs (i.e., CGACGTT (SEQ ID NO:57)). It should also be noted that ODNs containing no CpG (e.g., ODN 1982), runs of CpGs, or CpGs in bad sequence contexts (e.g., ODN 2010) had little or no stimulatory effect on NK activation.

TABLE 4

ODN induction of NK Lytic Activity (LU)

| ODN | Sequence (5'-3') | | LU |
|---|---|---|---|
| None | | | 0.01 |
| 1754 | ACCATGGACGATCTGTTTCCCCTC | (SEQ ID NO:26) | 0.02 |
| 1758 | TCTCCCAGCGTGCGCCAT | (SEQ ID NO:27) | 0.05 |
| 1761 | TACCGCGTGCGACCCTCT | (SEQ ID NO:28) | 0.05 |
| 1776 | ACCATGGACGAACTGTTTCCCCTC | (SEQ ID NO:29) | 0.03 |
| 1777 | ACCATGGACGAGCTGTTTCCCCTC | (SEQ ID NO:30) | 0.05 |
| 1778 | ACCATGGACGACCTGTTTCCCCTC | (SEQ ID NO:31) | 0.01 |
| 1779 | ACCATGGACGTACTGTTTCCCCTC | (SEQ ID NO:32) | 0.02 |
| 1780 | ACCATGGACGGTCTGTTTCCCCTC | (SEQ ID NO:33) | 0.29 |
| 1781 | ACCATGGACGTTCTGTTTCCCCTC | (SEQ ID NO:34) | 0.38 |
| 1823 | GCATGACGTTGAGCT | (SEQ ID NO:35) | 0.08 |
| 1824 | CACGTTGAGGGGCAT | (SEQ ID NO:36) | 0.01 |
| 1825 | CTGCTGAGACTGGAG | (SEQ ID NO:37) | 0.01 |
| 1828 | TCAGCGTGCGCC | (SEQ ID NO:38) | 0.01 |
| 1829 | ATGACGTTCCTGACGTT | (SEQ ID NO:39) | 0.42 |
| 1830[2] | RANDOM SEQUENCE | | 0.25 |
| 1834 | TCTCCCAGCGGGCGCAT | (SEQ ID NO:40) | 0.00 |
| 1836 | TCTCCCAGCGCGCGCCAT | (SEQ ID NO:41) | 0.46 |
| 1840 | TCCATGTCGTTCCTGTCGTT | (SEQ ID NO:42) | 2.70 |
| 1841 | TCCATAGCGTTCCTAGCGTT | (SEQ ID NO:43) | 1.45 |
| 1842 | TCGTCGCTGTCTCCGCTTCTT | (SEQ ID NO:44) | 0.06 |
| 1851 | TCCTGACGTTCCTGACGTT | (SEQ ID NO:45) | 2.32 |

[1]Lytic units (LU) were measured as described (8). Briefly, PBMC were collected from normal donors and spun over Ficoll, then cultured with or without the indicated ODN (which were added to cultures at 6 μg/ml) for 24 hr. Then their ability to lyse $^{51}$Cr-labeled K562 cells was determined. The results shown are typical of those obtained with several different normal human donors.
[2]This oligo mixture contained a random selection of all 4 bases at each position.

TABLE 5

Induction of NK LU by Phosphorothioate CpG ODN with Good Motifs

| ODN[1] | sequence (5'-3') | | expt. 1 | expt. 2 | expt. 3 |
|---|---|---|---|---|---|
| None | | | 0.00 | 1.26 | 0.46 |
| 1840 | TCCATGT<u>CG</u>TTCCTGT<u>CG</u>TT | (SEQ ID NO:42) | 2.33 | ND | ND |
| 1960 | TCCTGT<u>CG</u>TTCCTGT<u>CG</u>TT | (SEQ ID NO:46) | ND | 0.48 | 8.99 |
| 1961 | TCCATGT<u>CG</u>TTTTTGT<u>CG</u>TT | (SEQ ID NO:47) | 4.03 | 1.23 | 5.08 |
| 1962 | TCCTGT<u>CG</u>TTCCTTGT<u>CG</u>TT | (SEQ ID NO:13) | ND | 1.60 | 5.74 |
| 1963 | TCCTTGT<u>CG</u>TTCCTGT<u>CG</u>TT | (SEQ ID NO:48) | 3.42 | ND | ND |
| 1965 | TCCTGT<u>CG</u>TTTTTTGT<u>CG</u>TT | (SEQ ID NO:14) | 0.46 | 0.42 | 3.48 |
| 1966 | T<u>CG</u>T<u>CG</u>CTGTCT<u>CG</u>CTTCTT | (SEQ ID NO:44) | 2.62 | ND | ND |
| 1967 | T<u>CG</u>T<u>CG</u>CTGTCTGCCCTTCTT | (SEQ ID NO:15) | 5.82 | 1.64 | 8.32 |
| 1968 | T<u>CG</u>T<u>CG</u>CTGTTGT<u>CG</u>TTTCTT | (SEQ ID NO:16) | 3.77 | 5.26 | 6.12 |
| 1979[2] | TCCATGTZGTTCCTGTZGTT | (SEQ ID NO:42) | 1.32 | ND | ND |
| 1982 | TCCAGGACTTCTCTCAGGTT | (SEQ ID NO:50) | 0.05 | ND | 0.98 |
| 1990 | TCCATG<u>CG</u>TG<u>CG</u>TG<u>CG</u>TTTT | (SEQ ID NO:51) | 2.10 | ND | ND |
| 1991 | TCCATG<u>CG</u>TTG<u>CG</u>TTG<u>CG</u>TT | (SEQ ID NO:52) | 0.89 | ND | ND |
| 2002 | TCCA<u>CG</u>A<u>CG</u>TTTT<u>CG</u>A<u>CG</u>TT | (SEQ ID NO:53) | 4.02 | 1.31 | 9.79 |
| 2005 | T<u>CG</u>T<u>CG</u>TTGT<u>CG</u>TTGT<u>CG</u>TT | (SEQ ID NO:7) | ND | 4.22 | 12.75 |
| 2006 | T<u>CG</u>T<u>CG</u>TTTTGT<u>CG</u>TTTTGT<u>CG</u>TT | (SEQ ID NO:6) | ND | 6.17 | 12.82 |
| 2007 | T<u>CG</u>T<u>CG</u>TTGT<u>CG</u>TTTTGT<u>CG</u>TT | (SEQ ID NO:8) | ND | 2.68 | 9.66 |
| 2008 | G<u>CG</u>TG<u>CG</u>TTGT<u>CG</u>TTGT<u>CG</u>TT | (SEQ ID NO:9) | ND | 1.37 | 8.15 |
| 2010 | G<u>CG</u>G<u>CG</u>GG<u>CG</u>G<u>CG</u><u>CG</u><u>CG</u>CCC | (SEQ ID NO:54) | ND | 0.01 | 0.05 |
| 2012 | TGT<u>CG</u>TTTGT<u>CG</u>TTTGT<u>CG</u>TT | (SEQ ID NO:10) | ND | 2.02 | 11.61 |
| 2013 | TGT<u>CG</u>TTGT<u>CG</u>TTGT<u>CG</u>TTGT<u>CG</u>TT | (SEQ ID NO:55) | ND | 0.56 | 5.22 |
| 2014 | TGT<u>CG</u>TTGT<u>CG</u>TTGT<u>CG</u>TT | (SEQ ID NO:11) | ND | 5.74 | 10.89 |
| 2015 | T<u>CG</u>T<u>CG</u>T<u>CG</u>T<u>CG</u>TT | (SEQ ID NO:12) | ND | 4.53 | 10.13 |
| 2016 | TGT<u>CG</u>TTGT<u>CG</u>TT | (SEQ ID NO:56) | ND | 6.54 | 8.06 |

[1]PBMC essentially as described herein. Results are representative of 6 separate experiments; each experiment represents a different donor.
[2]This is the methylated version of ODN 1840; Z = 5-methyl cytosine LU is lytic units; ND = not done; CpG dinucleotides are underlined for clarity.

EXAMPLE 5

Identification of Phosphorothioate ODN with Optimal CPG Motifs for Activation of Human B Cell Proliferation The ability of a CpG ODN to induce B cell proliferation is a good measure of its adjuvant potential. Indeed, ODN with strong adjuvant effects in mouse studies also induce B cell proliferation. To determine whether the optimal CpG ODN for inducing B cell proliferation are the same as those for inducing NK cell activity, similar panels of ODN (Table 6) were tested. Many CpG ODN were stimulatory. ODN 2006 produced the most consistant stimulation (Table 6).

TABLE 6

Induction of human B cell proliferation by Phosphorothioate CpG ODN

| DN | sequence (5'–3') | | Stimulation Index[1] | | | | | |
|---|---|---|---|---|---|---|---|---|
| | | | expt. 1 | expt. 2 | expt. 3 | expt. 4 | expt. 5 | expt. 6 |
| 1840 | TCCATGTCGTTCCTGTCGTT | (SEQ ID NO:42) | 4 | ND | ND | ND | ND | 34 |
| 1841 | TCCATAGCGTTCCTAGCGTT | (SEQ ID NO:43) | 3 | ND | ND | ND | ND | ND |
| 1960 | TCCTGTCGTTCCTGTCGTT | (SEQ ID NO:46) | ND | 2.0 | 2.0 | 3.6 | ND | ND |
| 1961 | TCCATGTCGTTTTTGTCGTT | (SEQ ID NO:47) | 2 | 3.9 | 1.9 | 3.7 | ND | 37 |
| 1962 | TCCTGTCGTTCCTTGTCGTT | (SEQ ID NO:13) | ND | 3.8 | 1.9 | 3.9 | 5.4 | 35 |
| 1963 | TCCTTGTCGTTCCTGTCGTT | (SEQ ID NO:48) | 3 | ND | ND | ND | ND | ND |
| 1965 | TCCTGTCGTTTTTTGTCGTT | (SEQ ID NO:14) | 4 | 3.7 | 2.4 | 4.7 | 6.0 | 43 |
| 1967 | TCGTCGCTGTCTGCCCTTCTT | (SEQ ID NO:15) | ND | 4.4 | 2.0 | 4.5 | 5.0 | 36 |
| 1968 | TCGTCGCTGTTGTCGTTTCTT | (SEQ ID NO:16) | ND | 4.0 | 2.0 | 4.9 | 8.7 | 38 |
| 1982 | TCCAGGACTTCTCTCAGGTT | (SEQ ID NO:50) | 3 | 1.8 | 1.3 | 3.1 | 3.2 | 12 |
| 2002 | TCCACGACGTTTTCGACGTT | (SEQ ID NO:53) | ND | 2.7 | 1.4 | 4.4 | ND | 14 |
| 2005 | TCGTCGTTGTCGTTGTCGTT | (SEQ ID NO:7) | 5 | 3.2 | 1.2 | 3.0 | 7.9 | 37 |
| 2006 | TCGTCGTTTTGTCGTTTTGTCGTT | (SEQ ID NO:6) | 4 | 4.5 | 2.2 | 5.8 | 8.3 | 40 |
| 2007 | TCGTCGTTGTCGTTTTGTCGTT | (SEQ ID NO:8) | 3 | 4.0 | 4.2 | 4.1 | ND | 22 |
| 2008 | GCGTGCGTTGTCGTTGTCGTT | (SEQ ID NO:9) | ND | 3.0 | 2.4 | 1.6 | ND | 12 |
| 2010 | GCGGCGGGCGGCGCGCGCCC | (SEQ ID NO:54) | ND | 1.6 | 1.9 | 3.2 | ND | ND |
| 2012 | TGTCGTTTGTCGTTTGTCGTT | (SEQ ID NO:10) | 2 | 2.8 | 0 | 3.2 | ND | 33 |
| 2013 | TGTCGTTGTCGTTGTCGTTGTCGTT | (SEQ ID NO:55) | 3 | 2.3 | 3.1 | 2.8 | ND | 7 |
| 2014 | TGTCGTTGTCGTTGTCGTT | (SEQ ID NO:11) | 3 | 2.5 | 4.0 | 3.2 | 6.7 | 14 |
| 2015 | TCGTCGTCGTCGTT | (SEQ ID NO:12) | 5 | 1.8 | 2.6 | 4.5 | 9.4 | 1 |
| 2016 | TGTCGTTGTCGTT | (SEQ ID NO:56) | ND | 1.1 | 1.7 | 2.7 | 7.3 | 1 |

[1]Cells = human spleen cells stored at -70° C. after surgical harvest or PBMC collected from normal donors and spun over Ficoll. Cells were cultured in 96 well U-bottom microtiter plates with or without the indicated ODN (which were added to cultures at 6 μml). N = 12 experiments. Cells were cultured for 4–7 days, pulsed with 1 μCi of $^3$H thymidine for 18 hr before harvest and scintillation counting. Stimulation index = the ratio of cpm in wells without ODN to that in wells that had been stimulated throughout the culture period with the indicated ODN (there were no further additions of ODN after the cultures were set up). ND = not done

EXAMPLE 6

Identification of Phosphorothioate ODN that Induce Human IL-12 Secretion

The ability of a CpG ODN to induce IL-12 secretion is a good measure of its adjuvant potential, especially in terms of its ability to induce a Th1 immune response, which is highly dependent on IL-12. Therefore, the ability of a panel of phosphorothioate ODN to induce IL-12 secretion from human PBMC in vitro (Table 7) was examined. These experiments showed that in some human PBMC, most CpG ODN could induce IL-12 secretion (e.g., expt. 1). However, other donors responded to just a few CpG ODN (e.g., expt. 2). ODN 2006 was a consistent inducer of IL12 secretion from most subjects (Table 7).

TABLE 7

Induction of
human IL-12 secretion by Phosphorothioate CpG ODN

| ODN[1] | sequence (5'-3') | | IL-12 (pg/ml) expt. 1 | expt. 2 |
|---|---|---|---|---|
| None | | | 0 | 0 |
| 1962 | TCCTGTCGTTCCTTGTCGTT | (SEQ ID NO:13) | 19 | 0 |
| 1965 | TCCTGTCGTTTTTTGTCGTT | (SEQ ID NO:14) | 36 | 0 |
| 1967 | TCGTCGCTGTCTGCCCTTCTT | (SEQ ID NO:15) | 41 | 0 |
| 1968 | TCGCGCTGTTGTCGTTTCTT | (SEQ ID NO:16) | 24 | 0 |
| 2005 | TCGTCGTTGTCGTTGTCGTT | (SEQ ID NO:7) | 25 | 0 |
| 2006 | TCGTCGTTTTGTCGTTTGTCGTT | (SEQ ID NO:6) | 29 | 15 |
| 2014 | TGTCGTTGTCGTTGTCGTT | (SEQ ID NO:11) | 28 | 0 |
| 2015 | TCGTCGTCGTCGTT | (SEQ ID NO:12) | 14 | 0 |
| 2016 | TGTCGTTGTCGTT | (SEQ ID NO:56) | 3 | 0 |

[1]PBMC were collected from normal donors and spun over Ficoll, then cultured at $10^6$ cells/well in 96 well microtiter plates with or without the indicated ODN which were added to cultures at 6 μg/ml. Supernatants were collected at 24 hr and tested for IL-12 levels by ELISA as described in methods. A standard curve was run in each experiment, which represents a different donor.

EXAMPLE 7

Identification of B Cell and Monocyte/NK Cell-specific Oligonucleotides

CGp DNA can directly activate highly purified B cells and monocytic cells. There are many similarities in the mechanism through which CpG DNA activates these cell types. For example, both require NFkB activation as explained further below.

In further studies of different immune effects of CpG DNA, it was found that there is more than one type of CpG motif. Specifically, oligo 1668, with the best mouse B cell motif, is a strong inducer of both B cell and natural killer (NK) cell activation, while oligo 1758 is a weak B cell activator, but still induces excellent NK responses (Table 8).

induces a Th2 immune response (e.g., production of IgE antibody). IgE antibody production is known to be an important cause of asthma.

The immunized mice were then treated with oligonucleotides (30 μg in 200 μl saline by i.p. injection), which either contained an unmethylated CpG motif, i.e.,

TCCATGACGTTCCTGACGTT        (SEQ ID NO:39), or did not, i.e., control,

TCCATGAGCTTCCTGAGTCT        (SEQ ID NO:58).

Soluble SEA (10 μg in 25 μl of saline) was administered by intranasal instillation on days 14 and 21. Saline was used as a control.

Mice were sacrificed at various times after airway challenge. Whole lung lavage was performed to harvest airway

TABLE 8

Different CpG motifs stimulate optimal murine B cell and NK activation

| ODN Sequence | | B cell activation[1] | NK activation[2] |
|---|---|---|---|
| 1668 TCCATGACGTTCCTGATGCT | (SEQ ID NO:56) | 42,849 | 2.52 |
| 1758 TCTCCCAGCGTGCGCCAT | (SEQ ID NO:27) | 1,747 | 6.66 |
| NONE | | 367 | 0.00 |

CpG dinucleotides are underlined; oligonucleotides were synthesized with phosphorothioate modified backbones to improve their nuclease resistance.
[1]Measured by $^3$H thymidine incorporation after 48 hr culture with oligodeoxynucleotides at a 200 nM concentration as described in Example 1.
[2]Measured in lytic units.

EXAMPLE 8

Prevention of the Development of an Inflammatory Cellular Infiltrate and Eosinophilia in a Murine Model of Asthma Six to eight week old C56BL/6 mice (from The Jackson Laboratory, Bar Harbor, Me.) were immunized with 5,000 *Schistosoma mansoni* eggs by intraperitoneal (i.p.) injection on days 0 and 7. *Schistosoma mansoni* eggs contain an antigen (*Schistosoma mansoni* egg antigen (SEA)) that and alveolar inflammatory cells. Cytokine levels were measured from lavage fluid by ELISA. RNA was isolated from whole lung for Northern analysis and RT-PCR studies using CsCl gradients. Lungs were inflated and perfused with 4% paraformaldehyde for histologic examination.

Figure 8:
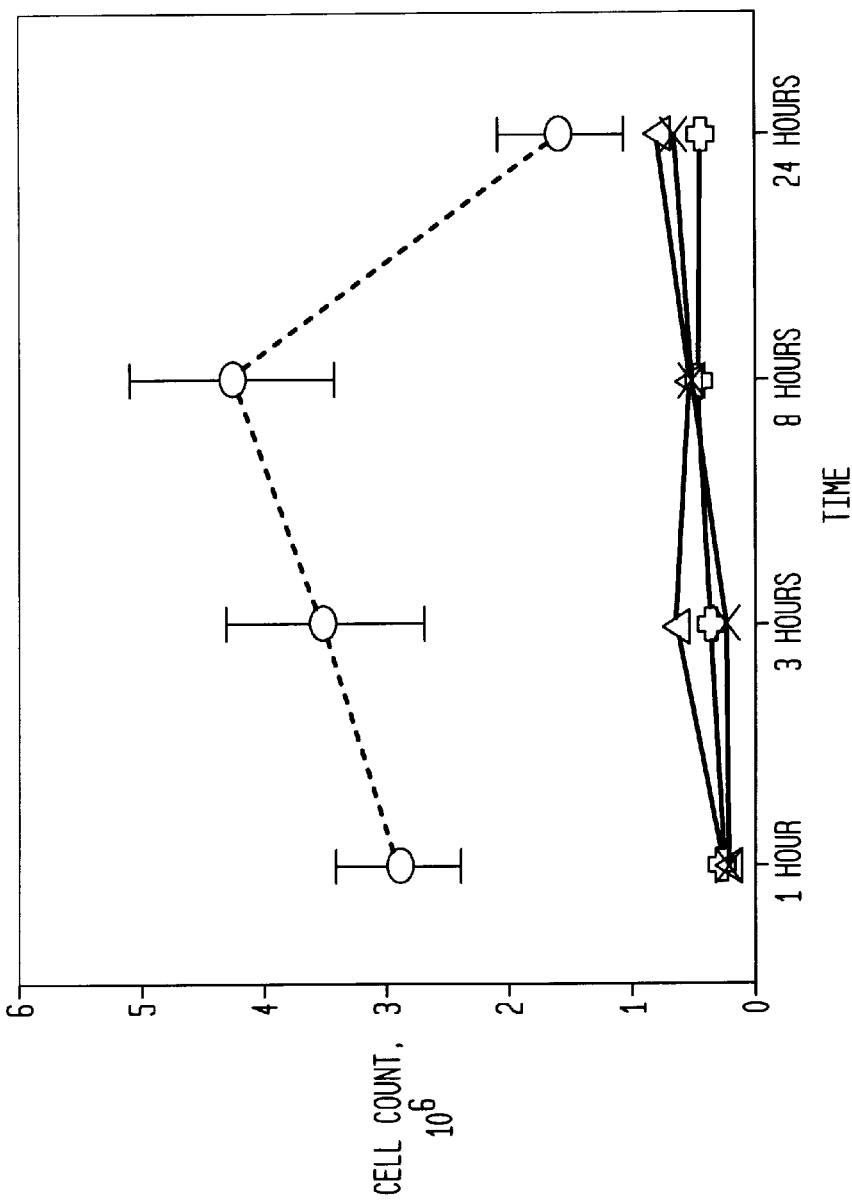
FIG. 8 is a graph plotting lung lavage cell count over time. The graph shows that when the mice are initially injected intraperitoneally (i.p.) with *Schistosoma mansoni* eggs "egg," which induces a Th2 immune response, and subsequently inhale *Schistosoma mansoni* egg antigen "SEA" (open circle), many inflammatory cells are present in the lungs. However, when the mice are initially given CpG ODN along with egg, the inflammatory cells in the lung are not as increased by subsequent inhalation of SEA (open triangles).

FIG. 8 shows that when the mice are initially injected with the eggs i.p., and then inhale the egg antigen (open circle), many inflammatory cells are present in the lungs. However, when the mice are initially given a nucleic acid containing an unmethylated CpG motif along with the eggs, the inflammatory cells in the lung are not increased by subsequent inhalation of the egg antigen (open triangles).

Figure 9:
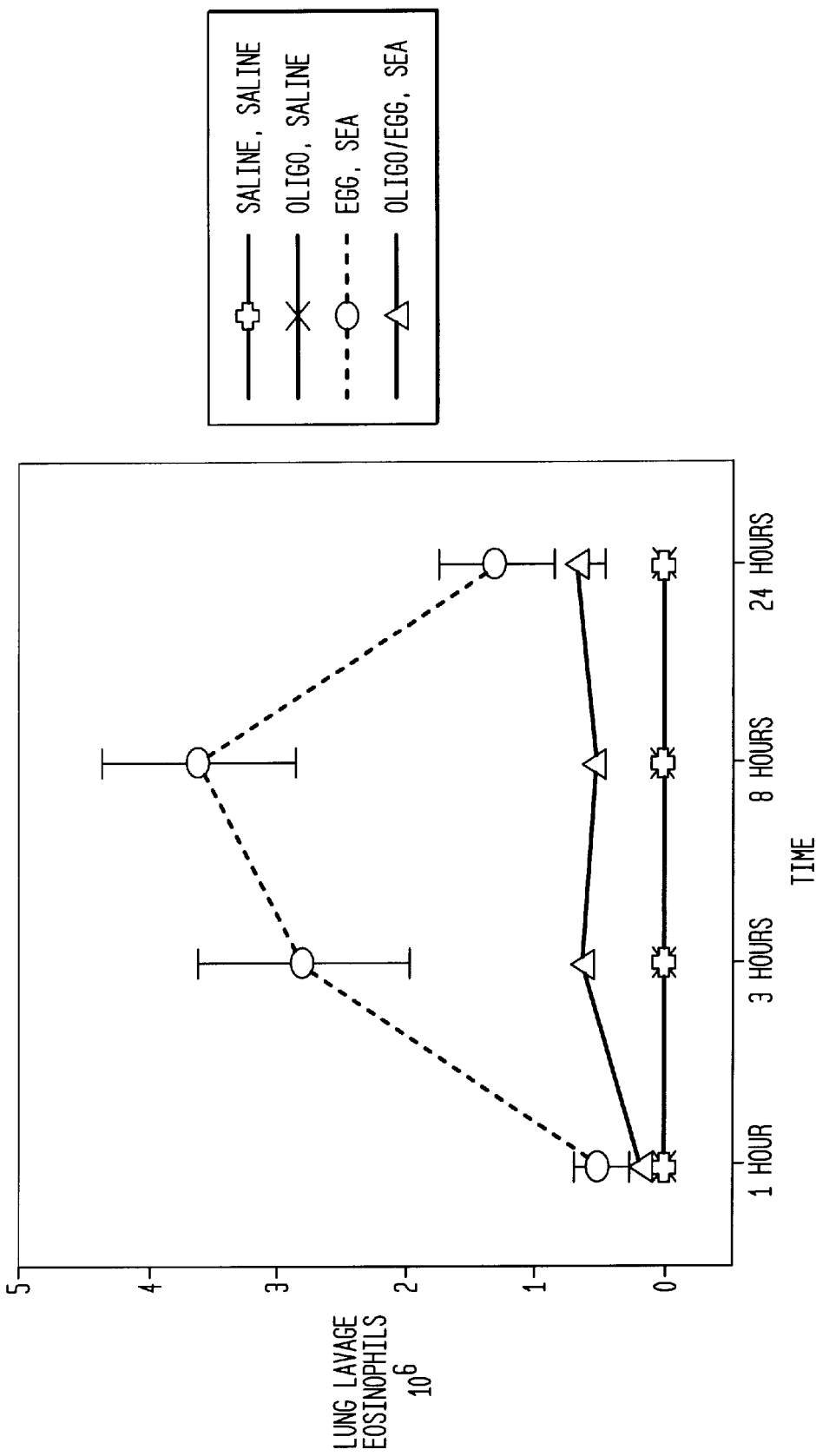
FIG. 9 is a graph plotting lung lavage eosinophil count over time. Again, the graph shows that when the mice are initially injected with egg and subsequently inhale SEA (open circle), many eosinophils are present in the lungs. However, when the mice are initially given CpG ODN along with egg, the inflammatory cells in the lung are not as increased by subsequent inhalation of the SEA (open triangles).

FIG. 9 shows that the same results are obtained when only eosinophils present in the lung lavage are measured. Eosinophils are the type of inflammatory cell most closely associated with asthma.

Figure 10:
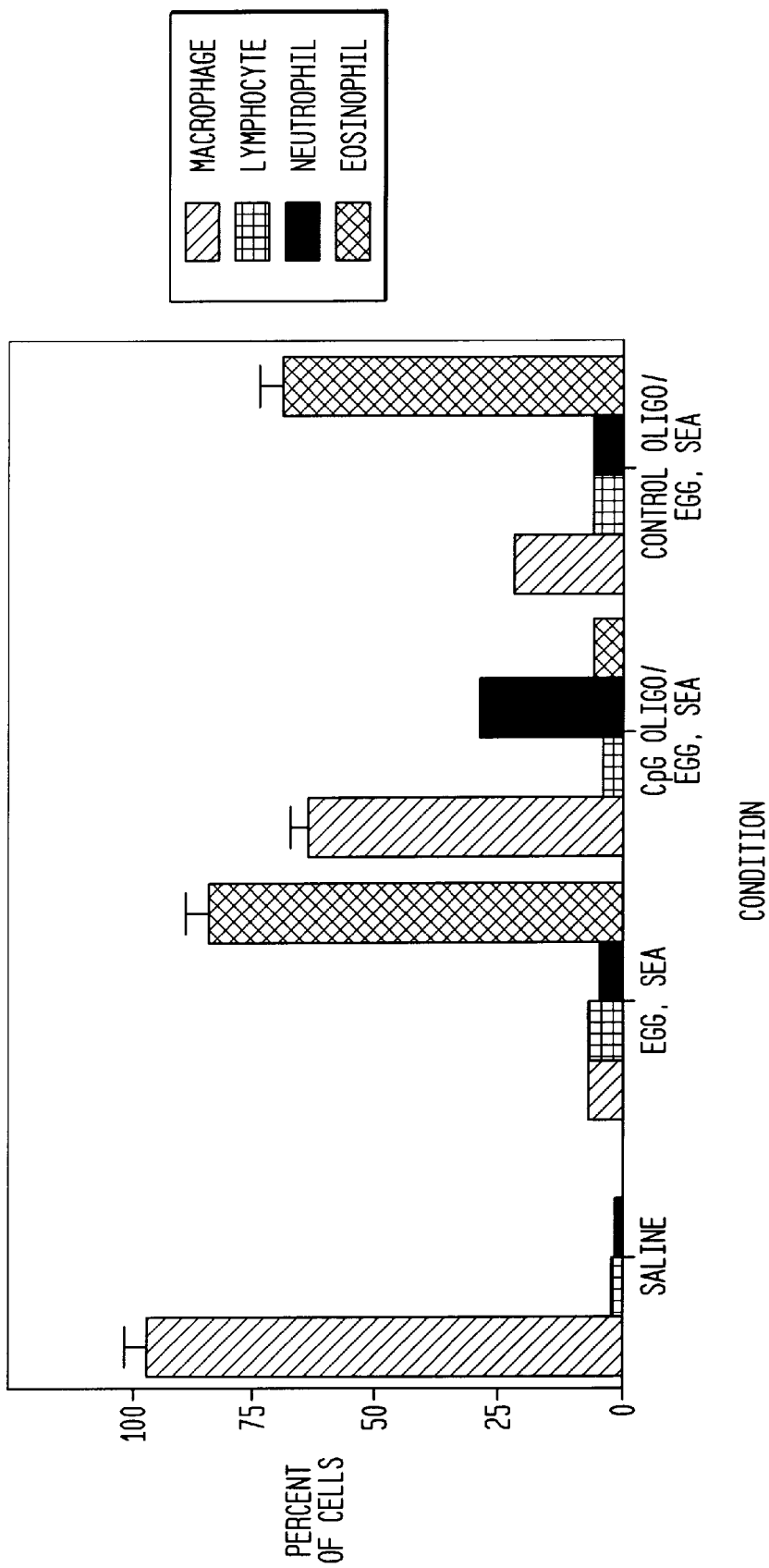
FIG. 10 is a bar graph plotting the effect on the percentage of macrophage, lymphocyte, neutrophil and eosinophil cells induced by exposure to saline alone; egg, then SEA; egg and CpG ODN, then SEA; and egg and control oligo, then SEA. When the mice are treated with the control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

FIG. 10 shows that when the mice are treated with a control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

Figure 11:
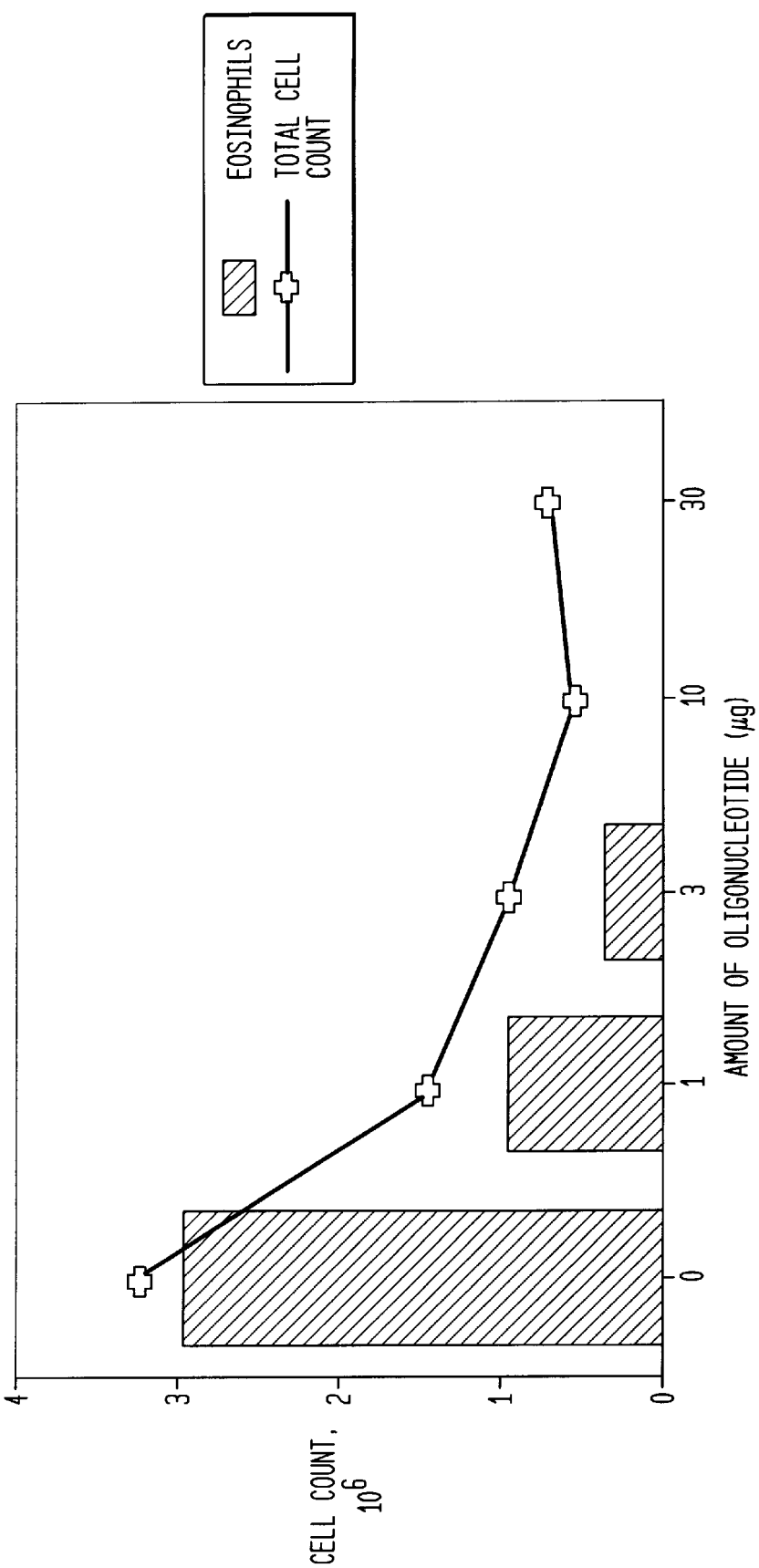
FIG. 11 is a bar graph plotting eosinophil count in response to injection of various amounts of the protective oligo SEQ ID NO: 10.

FIG. 11 shows that very low doses of oligonucleotide (<10 μg) can give this protection.

FIG. 12 shows that the resultant inflammatory response correlates with the levels of the Th2 cytokine IL-4 in the lung.

FIG. 13 shows that administration of an oligonucleotide containing an unmethylated CpG motif can actually redirect the cytokine response of the lung to production of Il12, indicating a Th1 type of immune response.

FIG. 14 shows that administration of an oligonucleotide containing an unmethylated CpG motif can also redirect the cytokine response of the lung to production of IFN-γ, indicating a Th1 type of immune response.

What is claimed is:

1. A method of treating a subject having or at risk of having an acute decrement in air flow, comprising:

administering to a subject having or at risk of having an acute decrement in air flow, wherein the acute decrement in air flow results from endotoxin exposure, a therapeutically effective amount of a nucleic acid sequence containing at least one unmethylated CpG.

2. The method of claim 1, wherein the nucleic acid sequence is from 8–30 bases in length.

3. The method of claim 1, wherein the subject is human.

4. The method of claim 1, wherein the acute decrement in airflow results from lipopolysaccharide (LPS) exposure.

5. The method of claim 1, wherein the nucleic acid sequence has a formula:

$$5'N_1X_1CGX_2N_2 3'$$ (SEQ ID NO:1)

wherein at least one nucleotide separates consecutive CpGs; $X_1$ is adenine, guanine, or thymidine; $X_2$ is cytosine or thymine, N is any nucleotide and $N_1+N_2$ is from about 0–26 bases.

6. The method of claim 5, wherein $N_1$ and $N_2$ do not contain a CCGG quadmer or more than one CGG trimer; and the nucleic acid sequence is from about 8–30 bases in length.

7. The method of claim 5, wherein said nucleic acid sequence is SEQ ID NO:2.

8. The method of claim 1, wherein the nucleic acid sequence has a formula:

$$5'N_1X_1X_2CGX_3X_4N_2 3'$$ (SEQ ID NO:3)

wherein at least one nucleotide separates consecutive CpGs; $X_1X_2$ is selected from the group consisting of GpT, GpG, GpA, ApT and ApA; $X_3X_4$ is selected from the group consisting of TpT or CpT; N is any nucleotide and $N_1+N_2$ is from about 0–26 bases.

9. The method of claim 8, wherein $N_1$ and $N_2$ do not contain a CCGG quadmer or more than one CCG or CGG trimer; and the nucleic acid sequence is from about 8–30 bases in length.

10. The method of claim 1 wherein the endotoxin exposure results from inhalation of LPS.

11. The method of claim 10 wherein the endotoxin exposure results in dust-induced airway disease.

12. The method of claim 10 wherein the endotoxin exposure results in LPS-induced asthma.

13. The method of claim 1 wherein the endotoxin exposure results in adult respiratory distress syndrome (ARDS).

14. The method of claim 1 wherein the endotoxin exposure results in endotoxemia.

15. The method of claim 1 wherein the endotoxin exposure results in systemic inflammatory response syndrome SIRS.

16. The method of claim 1 wherein the endotoxin exposure results in sepsis syndrome.

17. The method of claim 1 wherein the endotoxin exposure results in septic shock.

18. The method of claim 1 wherein the endotoxin exposure results in disseminated intravascular coagulation (DIC).

19. The method of claim 1 wherein the endotoxin exposure results in cardiac dysfunction.

20. The method of claim 1 wherein the endotoxin exposure results in organ failure, wherein the organ failure is selected from the group consisting of liver failure, brain failure, renal failure, and multi-organ failure.

21. The method of claim 1 wherein the endotoxin exposure results from a route of administration selected from the group consisting of administration of LPS-contaminated fluids and gram-negative infections.

22. The method of claim 1 wherein the subject is a subject who has been treated with chemotherapy.

23. The method of claim 1 wherein the subject is an immunocomprised subject.

24. The method of claim 1 wherein the nucleic acid sequence containing at least one unmethylated CpG is administered by a route selected from the group consisting of intravenous, parenteral, oral, implant and topical.

25. A method of inhibiting an inflammatory response in a subject having inhaled or at risk of having inhaled lipopolysaccharide (LPS), comprising:

administering to a subject having inhaled or at risk of having inhaled LPS, a therapeutically effective amount for inhibiting an inflammatory response of a nucleic acid sequence containing at least one unmethylated CpG.

26. The method of claim 25, wherein the nucleic acid sequence is from 8–30 bases in length.

27. The method of claim 25, wherein the subject is human.

28. The method of claim 25, wherein the nucleic acid sequence has a formula:

$$5'N_1X_1CGX_2N_23' \quad \text{(SEQ ID NO:1)}$$

wherein at least one nucleotide separates consecutive CpGs; $X_1$ is adenine, guanine, or thymidine; $X_2$ is cytosine or thymine, N is any nucleotide and $N_1+N_2$ is from about 0–26 bases.

29. The method of claim 28, wherein $N_1$ and $N_2$ do not contain a CCGG quadmer or more than one CGG trimer; and the nucleic acid sequence is from about 8–30 bases in length.

30. The method of claim 28, wherein said nucleic acid sequence is SEQ ID NO:2.

31. The method of claim 25, wherein the nucleic acid sequence has a formula:

$$5'N_1X_1X_2CGX_3X_4N_23' \quad \text{(SEQ ID NO:3)}$$

wherein at least one nucleotide separates consecutive CpGs; $X_1X_2$ is selected from the group consisting of GpT, GpG, GpA, ApT and ApA; $X_3X_4$ is selected from the group consisting of TpT or CpT; N is any nucleotide and $N_1+N_2$ is from about 0–26 bases.

32. The method of claim 31, wherein $N_1$ and $N_2$ do not contain a CCGG quadmer or more than one CCG or CGG trimer; and the nucleic acid sequence is from about 8–30 bases in length.

33. A method of modifying the level of a cytokine in a subject having inhaled or at risk of having inhaled lipopolysaccharide (LPS), comprising:

administering to a subject having inhaled or at risk of having inhaled LPS a therapeutically effective amount for modifying the level of a cytokine of a nucleic acid sequence containing at least one unmethylated CpG dinucleotide.

34. The method of claim 33, wherein the nucleic acid sequence is from 8–30 bases in length.

35. The method of claim 33, wherein the subject is human.

36. The method of claim 33, wherein said nucleic acid sequence is SEQ ID NO:2.

37. The method of claim 33, wherein the nucleic acid sequence has a formula:

$$5'N_1X_1CGX_2N_23' \quad \text{(SEQ ID NO:1)}$$

wherein at least one nucleotide separates consecutive CpGs; $X_1$ is adenine, guanine, or thymidine; $X_2$ is cytosine or thymine, N is any nucleotide and $N_1+N_2$ is from about 0–26 bases.

38. The method of claim 37, wherein $N_1$ and $N_2$ do not contain a CCGG quadmer or more than one CGG trimer; and the nucleic acid sequence is from about 8–30 bases in length.

39. The method of claim 33, wherein the nucleic acid sequence has a formula:

$$5'N_1X_1X_2CGX_3X_4N_23' \quad \text{(SEQ ID NO:3)}$$

wherein at least one nucleotide separates consecutive CpGs; $X_1X_2$ is selected from the group consisting of GpT, GpG, GpA, ApT and ApA; $X_3X_4$ is selected from the group consisting of TpT or CpT; N is any nucleotide and $N_1+N_2$ is from about 0–26 bases.

40. The method of claim 39, wherein $N_1$ and $N_2$ do not contain a CCGG quadmer or more than one CCG or CGG trimer; and the nucleic acid sequence is from about 8–30 bases in length.

41. The method of claim 33, wherein said modulation is a reduction in the level of said cytokine.

42. The method of claim 33, wherein said modulation is an increase in the level of said cytokine.

43. The method of claim 33, wherein said cytokine is selected from the group consisting of TNF-α, MIP-2, IL-10, IL-12, and interferon-γ.

* * * * *

UNITED STATES PATENT AND TRADEMARK OFFICE
CERTIFICATE OF CORRECTION

PATENT NO. : 6,214,806 B1
DATED : April 10, 2001
INVENTOR(S) : Krieg et al.

It is certified that error appears in the above-identified patent and that said Letters Patent is hereby corrected as shown below:

Title page,
Item [54], please replace "CPC" with -- CPG --.

Column 1,
Line 14, please delete the word "to" after the word "relates".
Line 41, please delete "asthmnatic", and insert -- asthmatic --.
Line 61, please delete "response", and insert -- responses --.

Column 5,
Line 19, before the words "pg/ml)", please insert -- ( --.

Column 6,
Line 46, please delete "tetrahyleneglycol", and insert -- tetraethyleneglycol --.

Column 12,
Line 6, after the word "taking", please delete ";".
Line 16, please delete "a.", and insert -- A. --.

Column 13,
Line 6, please delete "a", and insert -- an --.

Column 16,
Line 27, please delete "Multi robe", and insert -- Multiprobe --.

Column 18,
Table 1 footnote, please delete "*P>0.05", and insert -- *P<0.05 --.

Column 19,
Line 24, please delete "IL1-10", and insert -- IL-10 --.

Columns 21-22,
Table 3, after the number "1629", please delete "--------gtc--------", and insert -- -------gtc--------- --.
Table 3, after the number "1765", delete "--------X-----------", and insert -- -------X------------ --.
Table 3 footnote, line 2, please delete "methylcytosine", and insert -- 5-methyl-cytosine --.

UNITED STATES PATENT AND TRADEMARK OFFICE
CERTIFICATE OF CORRECTION

PATENT NO.    : 6,214,806 B1
DATED         : April 10, 2001
INVENTOR(S)   : Krieg et al.

It is certified that error appears in the above-identified patent and that said Letters Patent is hereby corrected as shown below:

Column 22,
Line 37, please delete "GTCGCT", and insert -- GTCGTT --.
Line 40, after the word "motif", please insert -- . --.
Line 54, before the word "preferably", please insert -- ( --.

Columns 23-24,
Table 5, after "1979", please delete "(SEQ ID NO: 42)" and insert
-- (SEQ ID NO: 67) --.

Column 28,
Line 32, please delete "(SEQ ID NO: 39)", and insert -- (SEQ ID NO: 62) --.

Column 30,
Line 11, please delete "Il 12", and insert -- IL-12 --.

Signed and Sealed this

Seventh Day of October, 2003

JAMES E. ROGAN
*Director of the United States Patent and Trademark Office*

SEQUENCE LISTING

```
<160> NUMBER OF SEQ ID NOS:  65

<210> SEQ ID NO 1
<211> LENGTH: 6
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (1)...(1)
<223> OTHER INFORMATION: any nucleotide
<221> NAME/KEY: misc_feature
<222> LOCATION: (6)...(6)
<223> OTHER INFORMATION: any nucleotide

<400> SEQUENCE: 1 ndcgyn                                                                     6

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
ataatcgacg ttcaagcaag                                                     20

<210> SEQ ID NO 3
<211> LENGTH: 8
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (1)...(1)
<223> OTHER INFORMATION: any nucleotide
<221> NAME/KEY: misc_feature
<222> LOCATION: (8)...(8)
<223> OTHER INFORMATION: any nucleotide

<400> SEQUENCE: 3 nrdcgytn                                                                   8

<210> SEQ ID NO 4
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 4
tccatgtcgc tcctgatgct                                           20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
tccatgtcgt tcctgatgct                                           20

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 6
tcgtcgtttt gtcgttttgt cgtt                                      24

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
tcgtcgttgt cgttgtcgtt                                           20

<210> SEQ ID NO 8
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 8
tcgtcgttgt cgttttgtcg tt                                        22

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
gcgtgcgttg tcgttgtcgt t                                         21

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 10 tgtcgttttgt cgtttgtcgt t                                        21
```

-continued

```
<210> SEQ ID NO 11
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 11
tgtcgttgtc gttgtcgtt                                                  19

<210> SEQ ID NO 12
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 12
tcgtcgtcgt cgtt                                                       14

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
tcctgtcgtt ccttgtcgtt                                                 20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
tcctgtcgtt ttttgtcgtt                                                 20

<210> SEQ ID NO 15
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 15
tcgtcgctgt ctgcccttct t                                               21

<210> SEQ ID NO 16
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 16
tcgtcgctgt tgtcgtttct t                                               21

<210> SEQ ID NO 17
<211> LENGTH: 7
<212> TYPE: DNA
<213> ORGANISM: Artificial Sequence
<220> FEATURE:
```

-continued

<223> OTHER INFORMATION: synthetic oligonucleotide

<400> SEQUENCE: 17 tgtcgtt                                                                  7

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
ataatagagc ttcaagcaag                                                   20

<210> SEQ ID NO 19
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 19
gctagacgtt agcgt                                                        15

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
gagaacgctg gaccttccat                                                   20

<210> SEQ ID NO 21
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 21
ggggtcaacg ttgacgggg                                                    19

<210> SEQ ID NO 22
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 22
ggggtcagtc ttgacgggg                                                    19

<210> SEQ ID NO 23
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 23
gctagacgtt agtgt                                                        15

```
<210> SEQ ID NO 24
<211> LENGTH: 15
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (8)...(8)
<223> OTHER INFORMATION: any nucleotide

<400> SEQUENCE: 24
gctagacntt agtgt                                                          15

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (8)...(8)
<223> OTHER INFORMATION: any nucleotide

<400> SEQUENCE: 25
tccatgtngt tcctgatgct                                                     20

<210> SEQ ID NO 26
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 26
accatggacg atctgtttcc cctc                                                24

<210> SEQ ID NO 27
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 27
tctcccagcg tgcgccat                                                       18

<210> SEQ ID NO 28
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 28
taccgcgtgc gaccctct                                                       18

<210> SEQ ID NO 29
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 29
accatggacg aactgtttcc cctc                                                24

<210> SEQ ID NO 30
```

```
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
accatggacg agctgtttcc cctc                                              24

<210> SEQ ID NO 31
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 31
accatggacg acctgtttcc cctc                                              24

<210> SEQ ID NO 32
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 32
accatggacg tactgtttcc cctc                                              24

<210> SEQ ID NO 33
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 33
accatggacg gtctgtttcc cctc                                              24

<210> SEQ ID NO 34
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 34
accatggacg ttctgtttcc cctc                                              24

<210> SEQ ID NO 35
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 35
gcatgacgtt gagct                                                        15

<210> SEQ ID NO 36
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 36
```

-continued

```
cacgttgagg ggcat                                                15

<210> SEQ ID NO 37
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 37
ctgctgagac tggag                                                15

<210> SEQ ID NO 38
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 38
tcagcgtgcg cc                                                   12

<210> SEQ ID NO 39
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 39
atgacgttcc tgacgtt                                              17

<210> SEQ ID NO 40
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 40
tctcccagcg ggcgcat                                              17

<210> SEQ ID NO 41
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 41
tctcccagcg cgcgccat                                             18

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
tccatgtcgt tcctgtcgtt                                           20

<210> SEQ ID NO 43
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 43
tccatagcgt tcctagcgtt                                                   20

<210> SEQ ID NO 44
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 44
tcgtcgctgt ctccgcttct t                                                 21

<210> SEQ ID NO 45
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 45
tcctgacgtt cctgacgtt                                                    19

<210> SEQ ID NO 46
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 46
tcctgtcgtt cctgtcgtt                                                    19

<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
tccatgtcgt ttttgtcgtt                                                   20

<210> SEQ ID NO 48
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 48
tccttgtcgt tcctgtcgtt                                                   20

<210> SEQ ID NO 49
<211> LENGTH: 6
<212> TYPE: DNA
<213> ORGANISM: Artificial Sequence
<220> FEATURE:
<223> OTHER INFORMATION: synthetic oligonucleotide

<400> SEQUENCE: 49 gtcgtt                                                                   6
```

```
<210> SEQ ID NO 50
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 50
tccaggactt ctctcaggtt                                              20

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 51
tccatgcgtg cgtgcgtttt                                              20

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 52
tccatgcgtt gcgttgcgtt                                              20

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
tccacgacgt tttcgacgtt                                              20

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
gcggcgggcg gcgcgcgccc                                              20

<210> SEQ ID NO 55
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 55
tgtcgttgtc gttgtcgttg tcgtt                                        25

<210> SEQ ID NO 56
<211> LENGTH: 13
<212> TYPE: DNA
<213> ORGANISM: Artificial Sequence
<220> FEATURE:
```

```
<223> OTHER INFORMATION: synthetic oligonucleotide

<400> SEQUENCE: 56
tgtcgttgtc gtt                                                          13

<210> SEQ ID NO 57
<211> LENGTH: 7
<212> TYPE: DNA
<213> ORGANISM: Artificial Sequence
<220> FEATURE:
<223> OTHER INFORMATION: synthetic oligonucleotide

<400> SEQUENCE: 57 cgacgtt                                                                 7

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 58
tccatgagct tcctgagtct                                                   20

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
cgcgcgcgcg cgcgcgcgcg                                                   20

<210> SEQ ID NO 60
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 60
tctcccagcg agcgccat                                                     18

<210> SEQ ID NO 61
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
ataatccagc ttgaaccaag                                                   20

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
tccatgacgt tcctgacgtt                                                   20
```

```
<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
ggggtcaacg ttgagggggg                                           20

<210> SEQ ID NO 64
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 64
ggggtctgtg cttttggggg g                                         21

<210> SEQ ID NO 65
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 65
ggcggcggcg gcggcggcgg                                           20
```